United States Patent [19]
Moloney et al.

[11] Patent Number: 5,856,452
[45] Date of Patent: Jan. 5, 1999

[54] OIL BODIES AND ASSOCIATED PROTEINS AS AFFINITY MATRICES

[75] Inventors: Maurice Moloney; Gijs van Rooijen; Joseph Boothe, all of Calgary, Canada

[73] Assignee: Sembiosys Genetics Inc., Calgary, Canada

[21] Appl. No.: 767,026

[22] Filed: Dec. 16, 1996

[51] Int. Cl.[6] .............................. C07K 1/14; C07K 1/22; C12S 3/14; C12S 13/00
[52] U.S. Cl. .......................... 530/412; 435/262; 435/270; 435/272; 435/277
[58] Field of Search ............................ 530/412; 435/262, 435/270, 272, 277

[56] References Cited

U.S. PATENT DOCUMENTS 5,474,925  12/1995  Maliyakal et al. .................... 435/172.3
5,538,946   7/1996  Crause et al. ............................ 514/12

FOREIGN PATENT DOCUMENTS

93/21320    10/1993  WIPO .
WO 96/21029  4/1996  WIPO .

OTHER PUBLICATIONS

Coughlin and Baclaski, *Biotechnology Progress,* 6:307–309, 1990.
Labrou and Clonis, *Journal of Biotechnology* 36:95–119, 1994.
Paradkar et al., *Biotechnol. Prog.,* 7:330–334, 1991
Parmenter et al., *Plant Molecular Biology,* 29:1167–1180, 1995.
Pireset al. *Biotechnol. Prog.* 12:290–301, 1996.
Schreuder et al., *Tibtech,* vol. 14, p. 115–120, 1996.
Van Rooijen and Moloney, *Plant Physiol* 109:1353–1361, 1995.
von Rooijen, Gijs J.H., "Molecular Biology of Oil Body Proteins in the Brassicaceae: Structure, Function and Biotechnological Applications," Ph.D. thesis, pp. 177–191, 1993.

*Primary Examiner*—Eric Grimes
*Attorney, Agent, or Firm*—Bereskin & Parr

[57] ABSTRACT

A method for the separation of a target molecule from a mixture is described. The method employs oil bodies and their associated proteins as affinity matrices for the selective, non-covalent binding of desired target molecules. The oil body proteins may be genetically fused to a ligand having specificity for the desired target molecule. Native oil body proteins can also be used in conjunction with an oil body protein specific ligand such as an antibody or an oil body binding protein. The method allows the separation and recovery of the desired target molecules due to the difference in densities between oil bodies and aqueous solutions.

25 Claims, 17 Drawing Sheets

FIGURE 1

```
  1 ATG GCG GAT ACA GCT AGA GGA ACC CAT CAC GAT ATC ATC GGC AGA GAC CAG TAC CCG ATG   60
  1  M   A   D   T   A   R   G   T   H   H   D   I   I   G   R   D   Q   Y   P   M    20

61 ATG GGC CGA GAC CGA CAG TAC CAG TAC ATG TCC GGA CGA GGA TCT GAC TAC TCC AAG TCT  120
 21  M   G   R   D   R   Q   Y   Q   Y   M   S   G   R   G   S   D   Y   S   K   S    40

121 AGG CAG ATT GCT GCA AAA GCT GTC ACT GCA ACT GCT GGT TCC CTT GTT CTC TCC TCC      180
 41  R   Q   I   A   A   K   A   V   T   A   T   A   G   S   L   V   L   S   S        60

181 AGC CTT ACC CTT GTT GGA ACT GTC ATA GCT CTC GTT GCA ACA CCT ATC ACC GGT ATC      240
 61  S   L   T   L   V   G   T   V   I   A   L   V   A   T   P   I   T   G   I        80

241 TTC AGC CCA ATC CTT GTC CCG GCT ATT GCC GCT CTC ATC CTC CTC TTC TCT CTT          300
 81  F   S   P   I   L   V   P   A   I   A   A   L   I   L   L   F   L              100

301 TCC TCT GGA GGG TTT GGC ATT GCC GCT ATA ACC GTT TTC TCT AGT GCA TAC GCA          360
101  S   S   G   G   F   G   I   A   A   I   T   V   F   S   S   A   Y   A          120

361 ACG GGA GAG CAC CCA CAG CAG GGA TCA GAC AAG TTG GAC AGT GCA AGG ATG AAG TTG GGA AGC 420
121  T   G   E   H   P   Q   Q   G   S   D   K   L   D   S   A   R   M   K   L   G   S 140

421 AAA GCT CAG GAT CTG AAA GAC AGA GCT CAG TAC TAC GGA CAG CAA CAT ACT GGT GGG GAA  480
141  K   A   Q   D   L   K   D   R   A   Q   Y   Y   G   Q   Q   H   T   G   G   E    160

481 CAT GAC CGT GAC CGT GGC ACT CGT GGT GGC CAG CAG CAC ACT ACT TAA                  522
161  H   D   R   D   R   G   T   R   G   G   Q   Q   H   T   T   *                    174
```

FIGURE 2 (P1)

```
   1 ctataccaacctcgtcttggtcacaccaggaactctctggtaagctagtccactcccagaaacaaccggcgccaaa    80
  81 ttgccggaattgctgacctgaagacgaacatcgtcgggtcctggggcgattgcggcggagatgggtcagctggg    160
 161 cttgaggacgagacccgatcgagtctgttgaaagttgttcattggattgtatacggagattggtcgtcgagaggtt    240
 241 tgagggaaaggacacaaatggggtttggctctctggagaaagagagtgcggctttagagagaattgagaggtttagagagagaga   320
 321 tgcggcggcgatgacggagagagacgacgaggacctgcattatcaaagcagtgacgtgtgaaattgaacttttaa    400
 401 gaggcagatagatttattgtatccattttcttcattgttctagaatgtcgcggaacaaatttaaactaaatcct    480
 481 aaattttctaattttgtgccaatagtggatggccgtatagaaggaatctattgaaggcccaacctattgaaggcccaacctactga  560
 561 cgagcccaaaggttcgtcgttttatgtttcggtttcgatgccaacgccacattctgagctaggcaaaaacaaacgt    640
 641 gtctttgaatagactcctcgttaacacatgcagcggctgcatggtgacgccattaacactgcctacaattgcatga    720
 721 tgtctccattgacacgtgacttctcgtctccttctaatatatctaacaacactcctacctcttccaaatatataca    800
 801 catcttttgatcaatctctcattcaaaatctcattctctagtaaacaagaacaaaaaa ATG GCG GAT ACA    873
                                                                  M   A   D   T     4
 874 GCT AGA GGA ACC CAT CAC GAT ATC ATC GGC AGA GAC CAG TAC CCG ATG ATG GGC CGA GAC    933
   5  A   R   G   T   H   H   D   I   I   G   R   D   Q   Y   P   M   M   G   R   D    24
 934 CGA GAC CAG TAC CAG TAC ATG TCC GGA CGA GGA TCT GAC TAC TCC AAG TCT AGG CAG ATT GCT    993
  25  R   D   Q   Y   Q   Y   M   S   G   R   G   S   D   Y   S   K   S   R   Q   I   A   44
 994 AAA GCT GCA ACT GCT GTC ACA GCT GGT GGT TCC CTC CTT GTT CTC CTC TCC AGC CTT ACC CTT   1053
  45  K   A   A   T   A   V   T   A   G   G   S   L   L   V   L   L   S   S   L   T   L   64
```

FIGURE 2 (P2)

```
1054 GTT GGA ACT GTC ATA GCT TTG ACT GTT GCA ACA CCT CTG CTC GTT ATC TTC AGC CCA ATC 1113
  65  V   G   T   V   I   A   L   T   V   A   T   P   L   L   V   I   F   S   P   I    84

1114 CTT GTC CCG GCT CTC ATC ACA GTT GCA CTC ATC ACC GGT TTT CTT TCC TCT GGA GGG 1173
  85  L   V   P   A   L   I   T   V   A   L   I   T   G   F   L   S   S   G   G        104

1174 TTT GGC ATT GCC GCT ATA ACC GTT TTC TCT TGG ATT TAC AA gtaagcacacattatcatcttact 1239
 105  F   G   I   A   A   I   T   V   F   S   W   I   Y   K                              118

1240 tcataatttttgtgcaatatgtgcatgcatgtgttgagccagtagcttttggatcaattttttgtcgaataacaaatgta 1319

1320 acaaataagaaattgcaaattctagggaacattggttaactaaatacgaaatttgacctagcttgaatgtgtctgt 1399

1400 gtatatcatctatataggtaaaatgcttggtatgataacctattgattgtgaatag G TAC GCA ACG GGA GAG 1470
                                                                Y   A   T   G   E   123

1471 CAC CCA CAG GGA TCA GAC AAG TTG GAC AGT GCA AGG ATG AAG TTG GGA AGC AAA GCT CAG 1530
 124  H   P   Q   G   S   D   K   L   D   S   A   R   M   K   L   G   S   K   A   Q    143

1531 GAT CTG AAA GAC AGA GAC GCT CAG CAA CAG ATC ACT GGT TGG GAA CAT GAC CGT 1590
 144  D   L   K   D   R   A   Q   Q   Q   I   T   G   W   E   H   D   R             163

1591 GAC CGT ACT CGT GGT GGC CAG CAG CAC ACT ACT GCG GAA GGG AGA ATC ACT TAC ACT GAC 1650
 164  D   R   T   R   G   G   Q   Q   H   T   T   A   E   G   R   I   T   Y   T   D    183

1651 TGT ACT GAA TCT CTC GGA CAG AAC CTC TGT GAA CTC TGT GGA TCT AAC GTT TGT GGA AAG GGA 1710
 184  C   T   E   S   L   G   Q   N   L   C   E   L   C   G   S   N   V   C   G   K   G  203

1711 AAC AAG TGT ATC CTC GGA TCT AAC GGA AAG GGA AAC CAG TGT GTT ACT GGA GAA GGA ACT 1770
 204  N   K   C   I   L   G   S   N   G   K   G   N   Q   C   V   T   G   E   G   T    223
```

FIGURE 2 (P3)

```
1771 CCA AAC CCA GAA TCT CAC AAC AAC GGA GAC TTC GAA GAA ATC CCT GAA GAA TAC CTC CAG 1830
 224  P   N   P   E   S   H   N   N   G   D   F   E   E   I   P   E   E   Y   L   Q   243
1831 TAA gtcgactctagacgcgatctcccgatcgttcaaacatttggcaataaagtttcttaagattgaatcctgttgccggt 1909
 244  *                                                                                244
1910 cttgcgatgattatcataataattctgttgaattacgttaagcatgtaatgcatgacgttatttat 1989
1990 gagatgggttttatgattagagtcccgcaattatacatttaatacgcgatagaaacaaaatatagcgcgcaaactagg 2069
2070 ataaattatcgcgcgcgggtgtcatctatgttactagatcGGAATTC                                 2115
```

FIGURE 8 (P1)

```
   1  gagctcaaatacgatctgatactgataacgtctagattttaggtaaagcaatcaatcacctgacgattcaaggtggt   80
  81  tggatcatgacgattccagaaaacatcaagcaagctctcaaagctacactctttgggatcatactgaactctaacaacct  160
 161  cgttatgtcccgtagtgccagtacagacatcctcgtaactcggattatgcacgatgccatggctataccaacctcgtc  240
 241  ttggtcacaccaggaactctctgtaagctagctccactcccagaaacaaccggcgccaaattgccggaattgctgacc  320
 321  tgaagacggaacatcgtcggtcctcgggtcctgagtcggcaaatgctgatggtcagcttgggcttgaggacgagacccga  400
 401  atcgagtctgttgaaaggttgttcattggattttgtatacggagattgtcgtcgagaggtttgagggaaaggacaaatg  480
 481  ggtttggctctgagaaagagagtgcggctttagagagagaattgagaggtttagagagatgcggcgatgacggg  560
 561  aggagagacgacgaggacctgcattatcaaagcagtgacgtggtgaactttaagaggcagatagattatt  640
 641  atttgtatccattcttcattgttctagaatgtcgcggaacaaatttaaaactaaatcctaaattttctaattttgt  720
 721  tgccaatagtggatatgtgggccgtatagaaggaatctattgaaggcccaaaccatactgacgagcccaaaggttcgtt  800
 801  ttgcgtttatgttcggttcgatgccaacgccacattctgagctaggcaaaaaacaaacgtgtctttgaatagactcct  880
 881  ctcgttaacacatgcagcggctgcatggtgacgccattaacacgtggcctacaattgcatgatgtctccattgacacgtg  960
 961  acttctcgtctccttttcttaatatatctcctagtaaacaggatcccctcgcggccgc ATG GCG GAT ACA GCT AGA ACC 1112
                                                              M   A   D   T   A   R   T   7
1113  CAT CAC GAT GTC ACA AGT CGA GAT CAG TAT CCC CGA GAC CGA GAT CCT CAT TGT CTA TCC ATG GAT ATC 1172
   8   H   H   D   V   T   S   R   D   Q   Y   P   R   D   R   D   Q   Y   S   M   I   27
```

FIGURE 8 (P2)

```
1173 GGT CGA GAC CGT GAC CAG TAC TCT ATG ATG GGC CGA GAC GAC CGA GAC CAG TAC AAC ATG TAT 1232
  28  G   R   D   R   D   Q   Y   S   M   M   G   R   D   D   R   D   Q   Y   N   M   Y    47

1233 GGT CGA GAC TAC TCC AAG TCT AGA CAG ATT GCT AAG GCT GTT ACC GCA GTC TAC ACG GCG GGT 1292
  48  G   R   D   Y   S   K   S   R   Q   I   A   K   A   V   T   A   V   Y   T   A   G    67

1293 GGG TCC CTC CTT GTC CTC CTC AGT TCC ACC CTT GTT GGT CTC GTG CCG ACT GTC ATT GCT TTG ACT GTT 1352
  68  G   S   L   L   V   L   L   S   S   T   L   V   G   L   V   P   T   V   I   A   L   T   V    87

1353 GCC ACT CCA TTT ATC GTT TTT AGC CCA ATC CTC GTG CCG GCT CTC ATC GCA GTA 1412
  88  A   T   P   F   I   V   F   S   P   I   L   V   P   A   L   I   A   V    107

1413 CTT CTC ATC ACT GGC TTT CTC TCT GGT GGG CAC GAG CAT GCA ATT GCA TCA GAT GCT ATA ACC GTC TTC 1472
 108  L   L   I   T   G   F   L   S   G   G   H   E   H   A   I   A   S   D   A   I   T   V   F    127

1473 TCC TGG ATC TAT AAG CTG GGA ACC AAA ATT AAA GAC CAG ACC CCA GGG TCA AGA GCT GAT AAG TTG GAC AGT 1532
 128  S   W   I   Y   K   L   G   T   K   I   K   D   Q   T   P   G   S   R   A   D   K   L   D   S    147

1533 GCA AGG ATG AAG CTG GGA ACC AAA GCT CAG GAT CGT GAC CGT ACT GGT GCC GCC TAC CAC ACT TAC GGA 1592
 148  A   R   M   K   L   G   T   K   A   Q   D   R   D   R   T   G   A   A   Y   H   T   Y   G    167

1593 CAG CAA CAT ACA GGT GGT GAG CAT GAT CCC ATG GAT GAC CGT AAC TGT TCC TGT AAA CAG CAG GAC TCC ACC 1652
 168  Q   Q   H   T   G   G   E   H   D   P   M   D   D   R   N   C   S   C   K   Q   Q   D   S   T    187

1653 CTC GTT CCA CGA GGA TCC ATG GAT CCC AAC TGT ACC TGT GCC GCC AGT CAG GAC AAA AAA TGC ACC 1712
 188  L   V   P   R   G   S   M   D   P   N   C   T   C   A   A   S   Q   D   K   K   C   T    207

1713 TGC GCC GGC TCC TGC AAG GAG AAA TGC ACC TCC TGC TGC AAG CAC TAC AGC TGC TGC 1772
 208  C   A   G   S   C   K   E   K   C   T   S   C   C   K   H   Y   S   C   C    227

1773 TCC TGC TGT CCT GTG GGC TGT GCC AAG TGT GCC CAG AAG TGC ATC AAA GGG GCG TCG 1832
 228  S   C   C   P   V   G   C   A   K   C   A   Q   K   C   I   K   G   A   S    247
```

FIGURE 8 (P3)

```
1833 GAC AAG TGC AGC TGC TGT GCC TGA gcggccgcgagggctgcagaatgagttccaagatgtttgtgacgaag 1904
 248  D   K   C   S   C   C   A   *                                                     255
1905 ttagttggttgtttttatggaactttgtttaagcttgtaatgtggaaagaacgtgtggcttttgtggttttaaatgttgg    1984
1985 tgaataaagatgttttcctttggattaactagtattttcctattggttcatggttttagcacacaacatttaaatatg      2064
2065 ctgttagatgatatgctgcctgctttattattactaccccctcacttcagttcaaagttgttgcaatgactctgtgt        2144
2145 agtttaagatcgagtgaagtagatttttgtctatatttattaggggtatttgatatgctaatggtaaacatggtttatga    2224
2225 cagcgtacttttggttatggttgacgtttccttttaaacattatagtagcgtccttgtcctgtgttcattggttga        2304
2305 acaaaggcacactcacttggagatgcgtctccactgatatttgaacaaagaattcggtacc                        2366
```

FIGURE 11

```
    BamHI
1   GGATCCCATG AAG CCC AGC AAC ACC AAG GTG GAC AAG AGA GTT GAG CTC AAA ACC CCA CTT    60
             1  M   K   P   S   N   T   K   V   D   K   R   V   E   L   K   T   P   L    18

61  GGT GAC ACA ACT CAC ACA TGC CCA CGG TGC CCA GAG CCC AAA TCT TGT GAC ACA CCT CCC   120
    19 G   D   T   T   H   T   C   P   R   C   P   E   P   K   S   C   D   T   P   P    38

121 CCG TGC CCA CGG TGC CCA GAG CCC AAA TCT TGT GAC ACA CCT CCC CCA TGC CCA CGG TGC   180
    39 P   C   P   R   C   P   E   P   K   S   C   D   T   P   P   P   C   P   R   C    58

181 CCA GAG CCC AAA TCT TGT GAC ACA CCT CCC CCG TGC CCA AGG TGC CCA GCA GCA CCT GAA CTC   240
    59 P   E   P   K   S   C   D   T   P   P   P   C   P   R   C   P   A   A   P   E   L    78

241 CTG GGA GGA CCG TCA GTC TTC CTC TTC CCC CCA AAA CCC ATC GAA GGT CGT GGA TCC           299
    79 L   G   G   P   S   V   F   L   F   P   P   K   P   I   E   G   R   G   S          97
                                             Factor Xa           BamHI
```

FIGURE 12 (P1)

```
            NcoI
  1 CTCC ATG GAT CAA CGC AAT GGT TTT ATC CAA AGC CTT AAA GAT GAT CCA AGC CAA AGT GCT  61
  1       M   D   Q   R   N   G   F   I   Q   S   L   K   D   D   P   S   Q   S   A   19

62 AAC GTT TTA GGT GAA GCT CAA AAA CTT CAA TCT CAA AAT GAC TCT CAA GCT GAT GCG CAA 121
 20  N   V   L   G   E   A   Q   K   L   Q   S   Q   N   D   S   Q   A   D   A   Q   39

122 CAA AAT AAC TTC AAC AAA GAT CAA CAA CAA AGC GCC TTC TAT GAA ATC TTG AAC ATG CCT AAC 181
 40  Q   N   N   F   N   K   D   Q   Q   Q   S   A   F   Y   E   I   L   N   M   P   N   59

182 TTA AAC GAA GCG CAA CGT AAC CAA TTC ATT CAA AGT CTT AAA GAC GAC CCA AGC CAA AGC 241
 60  L   N   E   A   Q   R   N   Q   F   I   Q   S   L   K   D   D   P   S   Q   S   79

242 ACT AAC GTT TTA GGT GAA GCT CAA AAA TTA AAC GAA TCT CAA GCA CCG AAA GAT AAC 301
 80  T   N   V   L   G   E   A   Q   K   L   N   E   S   Q   A   P   K   D   N   99

302 AAT TTC AAC AAA GAT CAA CAA AAT GCT TTC TAT GAA ATC TTG AAT ATG CCT AAC TTA AAC 361
100  N   F   N   K   D   Q   Q   N   A   F   Y   E   I   L   N   M   P   N   L   N  119

362 GAA GAA CAA CGC AAT GGT TTC ATC CAA AGC TTA AAA GAT GAC CCA AAA GCG GAT AAC AGT GCT AAC 421
120  E   E   Q   R   N   G   F   I   Q   S   L   K   D   D   P   K   A   D   N   S   A   N  139

422 CTA TTG TCA GAA CAA GCT AAA AAG TTA TTC TAT GAA TCT CAA GCA CCG AAA GCG GAT AAC TTC 481
140  L   L   S   E   Q   A   K   K   L   F   Y   E   S   Q   A   P   K   A   D   N   F  159

482 AAC AAA GAA CAA CAA AAT GCT TTC TAT GAA ATC TTA CAT TTA CCT AAC TTA AAC GAA GAA 541
160  N   K   E   Q   Q   N   A   F   Y   E   I   L   H   L   P   N   L   N   E   E  179

542 CAA CGC AAT GGT TTC ATC CAA AGC CTA AAA GAT GAC CCA AGC CAA AGC GCT AAC CTT TTA 601
180  Q   R   N   G   F   I   Q   S   L   K   D   D   P   S   Q   S   A   N   L   L  199
```

FIGURE 12 (P2)

```
602 GCA GAA GCT AAA AAG CTA AAT GAT GCT CAA GCA CCA AAA GCT GAC AAC AAA TTC AAC AAA 661
200  A   E   A   K   K   L   N   D   A   Q   A   P   K   A   D   N   K   F   N   K  219

662 GAA CAA CAA AAT GCT TTC TAT GAA ATT TTA CAT TTA CCT AAC TTA ACT GAA GAA CAA CGT 721
220  E   Q   Q   N   A   F   Y   E   I   L   H   L   P   N   L   T   E   E   Q   R  239

722 AAC GGC TTC ATC CAA AGC CTT AAA GAC CCG GGG AAT TCC CGG GGA TCC GTC GAC CTG 781
240  N   G   F   I   Q   S   L   K   D   P   G   N   S   R   G   S   V   D   L  259

782 CAG ATA ACA AAT TAG AAGCTTGC                                                804
260  Q   I   T   N   *      HindIII                                             264
```

OIL BODIES AND ASSOCIATED PROTEINS AS AFFINITY MATRICES

FIELD OF THE INVENTION

This invention relates to the use of oil bodies and their associated proteins as affinity matrices for the separation and purification of target molecules from mixtures.

BACKGROUND OF THE INVENTION

Within the general field of biotechnology, the ability to effectively separate and purify proteins of commercial value from complex sources such as living cells, blood serum, or fermentation broth is of critical importance. Applications in industry and research laboratories where purified or partly purified proteins are used are numerous and well documented in prior literature. See, for example, D. R. Meadon and G. Walsh in *Biotechnological Advances* 1994, 12: pp. 635–646.

The majority of currently employed protein purification techniques exploit the innate physical and chemical properties between proteins. One method of purifying proteins are the affinity-based purification techniques, which are unique in that, rather than relying on relatively nonspecific differences in physicochemical properties of proteins, they capitalize on the highly specific biological recognition between two molecular species which form an affinity pair. Binding of the two entities of the affinity pair occurs in almost all instances as a result of relatively weak chemical interactions, known as non-covalent bonds. Some recognized and commonly used affinity pairs include antibodies and their binding antigenic substances, nucleic acid binding proteins and nucleic acids, lipid binding proteins and lipids, lectins and carbohydrates, streptavidin/biotin complexes, protein A/immunoglobulin G complexes, and receptors and their binding substances.

In general, affinity based purification processes require that one member of the affinity pair is immobilized on a solid substrate or matrix that is insoluble in the fluid in which the other member of the pair resides. It is a further requirement that immobilization is accomplished in such a fashion that the capacity of the members of the affinity pair to recognize each other is not adversely affected by the immobilization procedure. The molecular species of the affinity pair bound to the matrix is generally referred to as the ligand, while the liquid soluble member is generally referred to as the target member. It is important to note that these definitions do not impose any restrictions in a strict chemical sense.

The vast majority of current immobilization techniques rely on physical or chemical approaches. Physical ligand immobilization involves adsorption or entrapment of the ligand to a suitable support, while the chemical mode of immobilization is characterized by the formation of strong crosslinks or covalent attachments between the ligand and the matrix.

It is a disadvantage of the currently available physical and chemical techniques for immobilizing ligands that production processes are frequently time consuming and expensive. This is mainly due to the fact that immobilization techniques require the separate production of matrix material and ligands, which in a subsequent step must be coupled. An alternative mode of immobilizing proteins is described in U.S. Pat. No. 5,474,925 which documents a biological production system for the immobilization of enzymes in the fibre of cotton plants. This patent discloses what is believed to be the first biologically produced enzyme immobilization system and allows a one step production of matrix and ligand.

Subsequent to immobilization of the ligand on the matrix, a variety of affinity based purification techniques may be employed to accomplish selective binding between the ligand and the target member. In the most widely used affinity based purification technique, affinity chromatography, a matrix containing a ligand is coated to, or packed on, the inside of a chromatographic column. A complex mixture containing the target member is then applied to the chromatographic column. Ideally, only the target molecules that specifically recognize the ligand bind in a non-covalent fashion to the chromatographic column, while all other molecular species present in the sample pass through the column. Other affinity-based purification technologies known to the prior art include, perfusion affinity chromatography, affinity repulsion chromatography, hyperdiffusion affinity chromatography, affinity precipitation, membrane affinity partitioning, affinity cross-flow ultrafiltration and affinity precipitation.

In affinity partitioning two solutions of substantially different densities are employed. The complex solution containing the target member is mixed with a solution of a different density containing the affinity ligand. Subsequent to mixing, the solutions are left to settle in order to permit the formation of two separate phases. Molecules tend to partition differentially between phases depending on their size, charge and specific interactions with the phase-forming solutions. Ligand-bound target protein selectively partitions to the phase containing the affinity ligand. For example, Coughlin and Baclaski in *Biotechnology Progress,* 1990 6: 307–309 reported the use of the biotin containing organic solution isooctane to transfer avidin from an aqueous solution to the isooctane solution. However, so far applications of affinity partitioning have been limited mainly due to the current lack of availability of suitable affinity matrix substances which can be employed in specific partitioning in two phase systems.

An important factor for the commercial development of biotechnology is the purification of bioproducts, which typically accounts for 50% or more of the total costs. Many purification steps rely on column or batch type separation procedures. In particular large scale high-separation techniques such as column chromatography affinity based purification techniques are costly. In addition, crude material is less suitable for either batch purification or column chromatography, as contaminants may foul up sedimented resins and plug columns. Thus, affinity matrices are often only employed in a later stage of purification processes where substantial purity is critical, where the proteins are present in extremely dilute concentrations, and/or where high value proteins are required, for example in diagnostic and therapeutic proteins. These and other topics related to the use of affinity technology in biotechnological processes have been reviewed by Labrou, N. and Clonis, Y. D. in the *Journal of Biotechnology* 36: 95–119 (1994).

There is a need in the art to develop a method for purifying biological products from complex mixtures. The present inventors have found that oil bodies and their associated proteins are useful in this regard.

Oil bodies are subcellular oil storage structures. Typically oil bodies accumulate in the seeds of higher plants and are enveloped by a phospholipid monolayer into which are embedded a limited amount of proteins referred to as oil body proteins. Oleosins are the predominant species of plant oil body protein present in the oil body phospholipid monolayer. Structurally oleosins are characterized in that they contain a highly lipophilic central portion which serves to anchor the protein in the phospholipid monolayer and more hydrophillic N- and C- termini which reside in the cytoplasm.

PCT application Publication No. WO 96/21029 describes the use of oil bodies for the preparation of recombinant proteins in plants. In this technology, the gene encoding the foreign protein is genetically fused to a plant oleosin gene, resulting in a fused protein product. Following biosynthesis the fusion protein is targeted to the oil body fraction of plant seeds. Floatation centrifugation is used to separate oil bodies from the aqueous portion of the seeds.

The present inventors have found that both oleosins fused to recombinant proteins as well as native oleosins are useful as affinity matrices.

SUMMARY OF THE INVENTION

According to the present invention, a novel versatile biological system for the production of affinity matrices is disclosed. The present invention provides for the novel use of oil bodies and their associated proteins as affinity matrices for the separation of desired target molecules.

In accordance with one aspect of the invention there is provided a method for the separation of a target molecule from a mixture comprising: 1) mixing (i) oil bodies that contain a sufficient portion of an oil body protein that can associate with the target molecule with (ii) a mixture containing the target molecule to allow the target molecule to associate with the oil bodies; and 2) separating the oil bodies associated with the target molecule from the mixture. If desired, the target molecule may be further separated from the oil bodies.

The oil body protein may associate with the target molecule through a ligand molecule. The ligand molecule is associated with the oil body protein and has affinity for the target. In one embodiment, the ligand is an antibody that binds the oil body protein. Such an antibody can be used to separate targets having affinity for the antibody such as anti-IgG antibodies or protein A. A bivalent antibody may also be prepared having binding specificities for both the oil body protein and the target. The antibody against the oil body protein may also be fused to a second ligand having affinity for the target.

In another embodiment, the ligand may be a protein that is produced as a fusion protein with the oil body protein (as described in WO 96/21029). In such a case, the fusion protein is targeted to and expressed on the oil bodies. In one example, the protein fused to the oil body protein may be hirudin and such a system can be used to purify thrombin.

The present invention offers an economical affinity matrix production system since, once proteins have been engineered to be able to be purified by oil body matrices, the production of large quantities of matrix thereafter is rendered inexpensive, as it involves agricultural cultivation of the oil body plant source.

Additional objects, features and advantages of the present invention will become clear after consideration of the accompanying drawings and the following detailed description of the invention.

BRIEF DESCRIPTION OF THE DRAWINGS

FIG. 1. The nucleotide and deduced amino acid sequence of the oleosin from *Arabidopsis thaliana* as shown in SEQ.ID.NO:1 and SEQ.ID.NO:2.

FIG. 2. Sequence of an Arabidopsis oleosin-hirudin fusion. Indicated are a portion of the oleosin genomic sequence (from base 1–1620 as reported in van Rooijen et al 1992, *Plant Mol. Biol.* 18: 1177–1179), a spacer sequence (base 1621–1635, underlined) and the synthetic DNA sequence encoding the mature hirudin variant-2 isoform (base 1636–1833, italicized) This gene fusion is regulated by the 5' upstream region of the Arabidopsis oleosin (bases 1–861) and the nopaline synthase termination sequence (base 1855–2109). The sequence is also shown in SEQ.ID.NO:3. The corresponding protein regions are also shown in SEQ.ID.NOS:3, 4 and 5.

FIG. 8. Sequence of an oleosin metallothionein fusion. Indicated are the coding sequence of a *B. napus* oleosin cDNA (bases 1092–1652, van Rooijen, 1993, Ph.D. Thesis, University of Calgary), a spacer sequence (bases 1653–1670, underlined) and the human metallothionein gene mt-II (bases 1671–1876, Varshney and Gedamu, 1984, *Gene*, 31: 135–145)). This gene fusion is regulated by an Arabidopsis oleosin promoter (bases 1–1072) and ubiquitin termination sequence (bases 1870–2361, ubi3'; Kawalleck et al., 1993, *Plant Mol. Biol.* 21: 673–684). The sequence is also shown in SEQ.ID.NO:6. The protein sequence is also shown in SEQ.ID.NO:7.

FIG. 11. Oligonucleotide primers used to amplify the sequence encoding IgG hinge domain from a human cDNA library. (The sequence is also shown in SEQ.ID.NO:8. The protein sequence is also shown in SEQ.ID.NO:9). Primer IgG001 5' *GGATCC*ATGAAGCCCAGCAACACCAAG 3' (SEQ.ID.NO:10), BamHI site (italicized), start-methionine (bold) and sequence identical to the IgG hinge domain region (Huck et al., 1986; *Febs Lett* 208: 221–230) (underlined). Primer IgG 002 5' *GGATCC*ACGACCTTC-GATGGGTTTTGGGGGGAAGAG 3', (SEQ.ID.NO:11), BamHI site (italicized), sequence encoding Fxa cleavage site (bold) and the sequence complementary to the IgG hinge domain region (Huck et al, 1986; Ibid) (underlined).

FIG. 12. Oligonucleotide primers used to amplify the sequence encoding a portion of the *S. aureus* protein A. (The sequence is also shown in SEQ.ID.NO:12. The protein sequence is shown in SEQ.ID.NO:13.) Primer BK266, 5' C TCC *ATG* GAT CAA CGC AAT GGT TTA TC 3', (SEQ.ID.NO:14), NcoI site (italicized) and sequence identical to a portion of the protein A gene as contained within vector pRIT2T (Pharmacia) (underlined). Primer BK267, 5'

Figure 3:
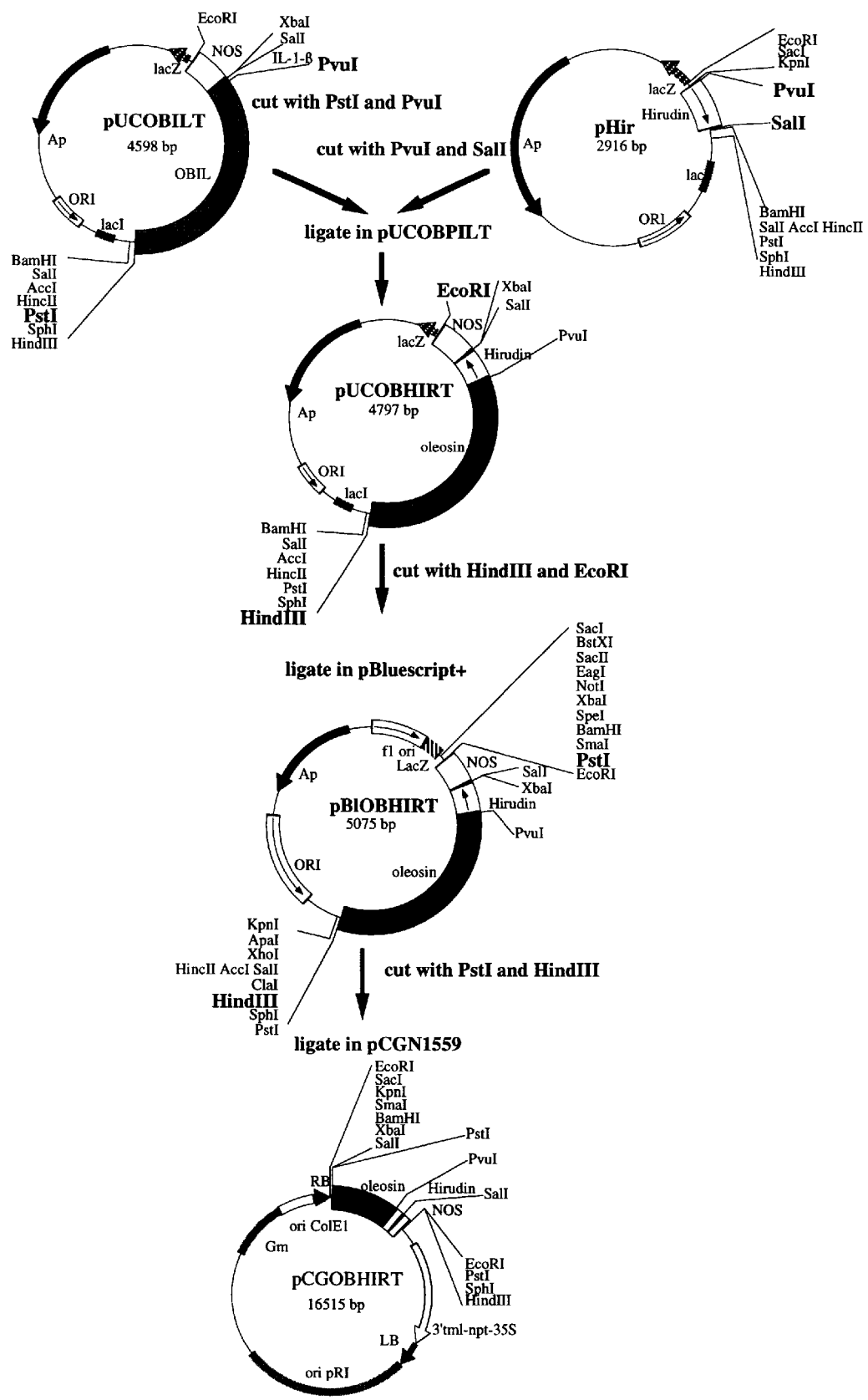
FIG. 3. Outline of the steps employed in the construction of pCGOBHIRT, containing the entire oleosin-hirudin construct.

GC AAG CTT CTA A*TTTGT TAT CTG CAG* GTC 3' (SEQ.ID.NO:15), HindIII site (italicized), stop codon (bold) and sequence complementary to a portion of the protein A gene as contained within pRIT2T (Pharmacia) (underlined). The PCR product was digested with NcoI and HindIII and ligated into pCGNOBPGUSA (Van Rooijen and Moloney 1995; *Plant Physiol* 109: 1353–1361) from which the NcoI-GUS-HindIII which had been removed.

DETAILED DESCRIPTION OF THE INVENTION

The present invention provides for the construction and use of a biological affinity matrix. This affinity matrix is suitable for the highly-efficient separation of specific targets, including proteins, carbohydrates, lipids, nucleic acids, cells and subcellular organelles, molecules and ions, from mixtures.

A. Targets

The term "target" as used herein denotes a desired molecule that one wants to purify or separate from a mixture such as a biological mixture. This technology is amenable for use with virtually any target for which a protein ligand can be obtained. Included within this group are both protein and non-protein targets. Possible ligand/target pairs include but are not limited to; protein subunit/subunit associations, antibodies/antigens, receptor protein/signals, nucleic acid binding proteins/nucleic acids; lectins/carbohydrates; lipid binding proteins/lipids; ion binding proteins/ions; and ligands to surface epitopes/cells or subcellular organelles. The target may be obtained from any natural source or may be synthesized chemically. If the target is a macromolecule such as a protein or nucleic acid it may also be produced in recombinant form using any suitable expression system such as bacteria, yeast, plant, insect, mammalian, etc.

B. Ligands

The term "ligand" used herein denotes a molecule that is capable of binding to, or associating with, both the target molecule and the oil body protein (discussed below). The affinity ligand proteins used for this methodology may be derived from naturally-occurring, known ligand pairs such as those listed above. Alternatively, they may be obtained through screening proteins extracted from cells or organisms, synthesized chemically or produced in libraries comprised of combinatorial peptide sequences, antibodies, or expressed DNA sequences.

In one embodiment, the ligand has natural affinity for the oil body protein. For example the ligand may be an antibody that has affinity for the oil body protein or another protein that binds the oil body protein.

In another embodiment the ligand is genetically fused to the oil body protein. In such a case, the sequence of the genes encoding them must be known or be obtainable. By obtainable it is meant that a DNA sequence sufficient to encode the protein ligand may be deduced from the known amino acid sequence. It is not necessary that the entire gene sequence of the ligand be used provided that a subsequence encoding the binding domain of the protein ligand is known.

Therefore, hereinafter "ligand" will be understood to mean either the complete sequence of, or the binding domain from, the specific ligand protein in question.

If the DNA sequence of the desired ligand is known, the gene may be synthesized chemically using an oligonucleotide synthesizer. Alternatively, the clone carrying the ligand gene may be obtained from either cDNA or genomic libraries containing the gene by probing with a labelled complementary DNA sequence. The gene may also be specifically amplified from the library using gene-specific oligonucleotide primers and the PCR. If the DNA sequence of the desired ligand is not known, then a partial amino acid sequence may be obtained through N-terminal sequencing of the protein (Matsudaira 1987; *J. Biol. Chem.* 262: 10035–10038). Labeled probes may be synthesized based upon the DNA sequences deduced from this amino acid sequence and used to screen cDNA or genomic libraries as described above. The clone carrying the gene may also be identified from a cDNA expression library by probing either with antibodies raised against the protein ligand, or with the target protein.

Ligands may also be uncovered by probing complex mixtures of proteins with the target. The target can be immobilized on a support matrix and used to screen proteins extracted from cells and tissues or synthesized chemically. Following binding between the ligand protein and the immobilized target, the matrix is separated from the solution and washed. The protein ligand is subsequently eluted from the matrix and the sequence determined as described above. Alternatively, recombinant protein libraries produced by phage display, such as those comprised of combinatorial peptide sequences (Smith, 1985; *Science* 228: 1315–1317) or antibody repertoires (Griffiths et al., 1994, *EMBO J.* 13: 3245–3260, Nissim et al., 1994, *EMBO J.* 13: 692–698) can be screened with the immobilized target. In this case, binding between the protein ligand and the target would enable separation and recovery of the phage expressing the ligand from the large, complex population of phage encoding non-binding proteins. A two-hybrid system such as that in yeast (Fields and Sternglanz, 1994; *Trends Genet.* 10: 286–292) might also be used to identify a ligand from an expressed cDNA library. Here, a gene fusion is constructed between the sequence encoding the target protein and that of a DNA binding protein. Cells containing this construct are transformed with constructs from a cDNA library where the sequences have been fused to that of a transcriptional activator. Binding between ligands derived from the cDNA library with the target protein allows transcription of a reporter gene to occur. Clones expressing the ligand are then recovered.

To specifically uncover a ligand to oil bodies, a complete or partial oleosin protein may be used as target in any of the above methods. Alternatively, it may be possible to employ intact oil bodies for screening protein extracts, synthetic peptides or phage display libraries. In this case, the oil body would serve both as target and immobilization matrix. Using this approach, a wider variety of ligands may be uncovered; that exhibit affinity not only to oleosins, but to other epitopes present on oil bodies.

In any of the above approaches, once the gene encoding the ligand has been identified, its DNA sequence can be determined using standard methods. This sequence may then be fused to oleosin, target protein or other ligand sequences and introduced into suitable cloning and/or expression vectors.

C. Oil Bodies/Oil Body Proteins

Oil bodies are small, spherical, subcellular organelles encapsulating stored triacylglycerides, an energy reserve used by many plants. Although they are found in most plants and in different tissues, they are particularly abundant in the seeds of oilseeds where they range in size from under one micron to a few microns in diameter. Oil bodies are comprised of the triacylglycerides surrounded by a half-unit membrane of phospholipids and embedded with a unique type of protein known as oleosin. Oleosins have been cloned and sequenced from many plant sources including corn, rapeseed, carrot and cotton. The oleosin protein appears to be comprised of three domains; the two ends of the protein, N- and C-termini, are largely hydrophillic and reside on the surface of the oil body exposed to the cytosol while the highly hydrophobic central core of the oleosin is firmly anchored within the membrane and triacylglyceride. Oleosins from different species represent a small family of proteins showing considerable amino acid sequence conservation, particularly in the central region of protein. Within an individual species, a small number of different isoforms may exist. For the purpose of this invention, the term "oil body" will be understood to include any or all of the triacylglyceride, phospholipid or protein components present in the complete structure.

Properties and Configurations of Oil Body Affinity Matrices

Oil bodies from individual species exhibit a roughly uniform size and density which is dependent in part upon the precise protein/phospholipid/triacylglyceride composition. As a result, they may be simply and rapidly separated from liquids of different densities in which they are suspended. For example, in aqueous media where the density is greater than that of the oil bodies, they will float under the influence of gravity or applied centrifugal force. In 95% ethanol where the density is less than that of the oil bodies, they will sediment under the same conditions. Oil bodies may also be separated from liquids and other solids present in solutions or suspensions by methods that fractionate on the basis of size. For example, the oil bodies from *B. napus* are minimal, approximately 0.5 μm in diameter, and thus may be separated from smaller components using a membrane filter with a pore size less than this diameter.

It is an advantage of the present invention that target substances can be purified or removed from complex mixtures through non-covalent association with oil bodies followed by oil body separation. In one form of the invention, ligand protein sequences are genetically fused to oleosin. In particular, a chimeric DNA sequence may be prepared that encodes an oil body protein-ligand fusion protein and consists of (a) a DNA sequence encoding a sufficient portion of an oil body protein to provide targeting of the fusion protein to the oil bodies and (b) a DNA sequence encoding a sufficient portion of the ligand protein to provide binding of the target. The inventors have determined that, in general, the N-terminus and the hydrophobic core of an oil body protein are sufficient to provide targeting of the fusion protein to the oil bodies. In particular, for oleosins derived from the plant *Arabidopsis thaliana* amino acids 2 through 123 (as shown in SEQ.ID.NO:1) are sufficient in this regard.

The ligand may be fused to either the N- and/or C-terminal end of the oleosin. It may also be possible to construct an internal fusion between the ligand and oleosin or to fuse the ligand between two oleosin proteins. Oil bodies containing the fusion protein obtained from the seeds of transgenic plants comprise an immobilized matrix for the non-covalent or affinity separation of targets.

In another form of the invention, ligands with natural affinity for oil bodies are employed. Examples of such ligands include anti-oil body protein antibodies and oil body binding proteins. The advantage of this approach is that a genetically-engineered oleosin is not required. Oil bodies prepared from non-transgenic seeds act as the affinity matrix, potentially enabling a greater proportion of the total surface area to participate in binding and thereby increasing the total binding capacity per unit of oil body matrix.

A number of different oil body-ligand configurations are possible. Targets with inherent affinity for a specific ligand proteins such as hirudin to thrombin or heavy metals to metallothionein, may be purified with oil bodies containing that ligand fused to an oleosin. Alternatively, a protein target may also be purified with an oil body affinity matrix by fusing the target to an oil body-specific ligand or to a ligand complimentary to that fused to an oleosin. If desired, a protease recognition site or chemical cleavage site may be engineered between the ligand and the target protein to enable proteolytic removal of the ligand from the target protein in the course of purification. A multivalent ligand may also be constructed, such as a bivalent single-chain antibody, in which one domain of the ligand has an affinity for an oil body and the other domain(s) exhibits affinity for the target. In this case, neither the oil body nor the target molecule need to be covalently fused to a ligand. Also, concatemers of ligands may be used to increase the affinity of a matrix for a target, or the sequence of a ligand may be mutated to reduce the affinity for a target when such conditions are desirable. Further, mixtures of different ligands may be fused to recover/remove different types of targets simultaneously. Fusions between different ligands may also be constructed to form bridges between different types of targets or between targets and the oil body affinity matrix. Binding to the affinity matrix may also be achieved by forming bridges between ligand or ligand and target sequences, such as $Zn^{++}$ ions bridging between polyhistidine sequences.

There are several advantages associated with the use of oil body affinity matrices that make them attractive as purification tools. The flexibility in design that is possible through the different configurations described above, enables a matrix to be constructed to best meet the requirements for a specific target. Also, production of the matrix as part of a natural biological process in seeds is extremely cost-effective, since purification and immobilization of the ligand are not necessary. In the case of oleosin-ligand fusions, the ligand is immobilized on the oil body as a result of oleosin targeting within the cell, while oil body-specific ligands will naturally associate with the matrix while present in complex mixtures. Natural immobilization of the ligand on the matrix may also be advantageous in that it eliminates the requirement for chemically cross-linking that may compromise the affinity of the ligand for the target. Finally, oil body affinity matrices offer a unique and attractive purification option particularly for large scale operations. The ability to separate the matrix through flotation as a loose suspension enables it to be employed with crude material containing what might otherwise be prohibitive amounts of particulate contaminants. The presence of these contaminants will often foul and block conventional solid matrices applied in columns or batch suspensions limiting their use at early stages in the purification process.

Cloning and Transformation Vectors

Two types of vectors are routinely employed. The first type of vector is used for the genetic-engineering and assembly of constructs and typically consists of a backbone such as found in the pUC family of vectors, enabling replication in easily-manipulated and maintained gram negative bacteria such as *E. coli*. The second type of vector typified by the Ti and Ri plasmids, specify DNA transfer functions and are used when it is desired that the constructs be introduced into the plant and stably integrated into its genome via Agrobacterium-mediated transformation.

A typical construct consists, in the 5' to 3' direction, of a regulatory region complete with a promoter capable of directing expression in plants (preferably seed-specific expression), a protein coding region, and a sequence containing a transcriptional termination signal functional in plants. The sequences comprising the construct may be either natural or synthetic or any combination thereof.

Both non-seed specific promoters, such as the 35-S CaMV promoter (Rothstein et al., 1987; *Gene* 53: 153–161) and seed-specific promoters such as the phaseolin promoter (Sengupta-Gopalan et al., 1985; PNAS USA 82: 3320–3324) or the Arabidopsis 18 kD oleosin (Van Rooijen et al., 1992; Plant Mol. Biol. 18: 1177–1179) promoters may be used. In addition to the promoter, the regulatory region contains a ribosome binding site enabling translation of the transcripts in plants and may also contain one or more enhancer sequences, such as the AMV leader (Jobling and Gehrke 1987; Nature 325: 622–625), to increase the expression of product.

The coding region of the construct will typically be comprised of sequences encoding a ligand fused in frame to an oleosin and ending with a translational termination codon. The sequence for the oleosin may be comprised of any DNA sequence, or part thereof, natural or synthetic, sufficient to encode a protein that can be correctly targeted to, and stably expressed on, an oil body. A detailed description of the characteristics of such a sequence has been reported previously in PCT Patent Appl. WO 96/21029. The sequence may also include introns. The ligand-encoding region may in turn be comprised of any individual, or combination of, ligand sequences identified as described above. If desired, a protease or chemical recognition site may be engineered between the ligand and the target protein to enable proteolytic removal of the ligand from the target protein in the course of purification.

The region containing the transcriptional termination signal may comprise any such sequence functional in plants such as the nopaline synthase termination sequence and additionally may include enhancer sequences to increase the expression of product.

The various components of the construct are ligated together using conventional methods, typically into a pUC-based vector. This construct may then be introduced into an *Agrobacterium vector* and subsequently into host plants, using one of the transformation procedures outlined below.

Transformation of Plants

A variety of techniques is available for the introduction of DNA into host cells. For example, the chimeric DNA constructs may be introduced into host cells obtained from dicotyledonous plants, such as tobacco, and oleaginous species, such as *B. napus* using standard Agrobacterium vectors; by a transformation protocol such as that described by Moloney et al., 1989, (*Plant Cell Rep.*, 8: 238–242) or Hinchee et al., 1988, (*Bio/Technol.*, 6: 915–922); or other techniques known to those skilled in the art. For example, the use of T-DNA for transformation of plant cells has received extensive study and is amply described in EPA Ser. No. 120,516; Hoekema et al., 1985, (Chapter V, In: *The Binary Plant Vector System* Offset-drukkerij Kanters B. V., Alblasserdam); Knauf, et al., 1983, (*Genetic Analysis of Host Range Expression by Agrobacterium*, p. 245, In Molecular Genetics of the Bacteria-Plant Interaction, Puhler, A. ed., Springer-Verlag, NY); and An et al., 1985, (*EMBO J.*, 4: 277–284). Conveniently, explants may be cultivated with *A. tumefaciens* or *A. rhizogenes* to allow for transfer of the transcription construct to the plant cells. Following transformation using Agrobacterium the plant cells are dispersed in an appropriate medium for selection, subsequently callus, shoots and eventually plantlets are recovered. The Agrobacterium host will harbour a plasmid comprising the vir genes necessary for transfer of the T-DNA to the plant cells. For injection and electroporation, (see below) disarmed Ti-plasmids (lacking the tumour genes, particularly the T-DNA region) may be introduced into the plant cell.

The use of non-Agrobacterium techniques permits the use of the constructs described herein to obtain transformation and expression in a wide variety of monocotyledonous and dicotyledonous plants and other organisms. These techniques are especially useful for species that are intractable in an Agrobacterium transformation system. Other techniques for gene transfer include biolistics (Sanford, 1988, *Trends in Biotech.*, 6: 299–302), electroporation (Fromm et al., 1985, *Proc. Natl. Acad. Sci. USA*, 82: 5824–5828; Riggs and Bates, 1986, *Proc. Natl. Acad. Sci. USA* 83: 5602–5606) or PEG-mediated DNA uptake (Potrykus et al., 1985, *Mol. Gen. Genet.*, 199: 169–177).

In a specific application, such as to *B. napus*, the host cells targeted to receive recombinant DNA constructs typically will be derived from cotyledonary petioles as described by Moloney et al., (1989, *Plant Cell Rep.*, 8: 238–242). Other examples using commercial oil seeds include cotyledon transformation in soybean explants (Hinchee et al., 1988. *Bio/Technology*, 6: 915–922) and stem transformation of cotton (Umbeck et al., 1981, *Bio/Technology*, 5: 263–266).

Regeneration and Analysis of Transgenic Plants

Following transformation, the cells, for example as leaf discs, are grown in selective medium. Once shoots begin to emerge, they are excised and placed onto rooting medium. After sufficient roots have formed, the plants are transferred to soil. Putative transformed plants are then tested for presence of a marker. Southern blotting is performed on genomic DNA using an appropriate probe, for example an *A. thaliana* oleosin gene, to show that integration of the desired sequences into the host cell genome has occurred.

The expression cassette will normally be joined to a marker for selection in plant cells. Conveniently, the marker may be resistance to a herbicide, e.g. phosphinothricin or glyphosate, or more particularly an antibiotic, such as kanamycin, G418, bleomycin, hygromycin, chloramphenicol, or the like. The particular marker employed will be one which will allow for selection of transformed cells compared with cells lacking the introduced recombinant DNA.

The fusion peptide in the expression cassette constructed as described above, expresses at least preferentially in developing seeds. Accordingly, transformed plants grown in accordance with conventional ways, are allowed to set seed. See, for example, McCormick et al. (1986, *Plant Cell Reports*, 5: 81–84). Northern blotting can be carried out using an appropriate gene probe with RNA isolated from tissue in which transcription is expected to occur, such as a seed embryo. The size of the transcripts can then be compared with the predicted size for the fusion protein transcript.

Oil body proteins are then isolated from the seed and analyses performed to determine that the fusion peptide has been expressed. Analyses can be for example by SDS-PAGE. The fusion peptide can be detected using an antibody to the oleosin portion of the fusion peptide. The size of the fusion peptide obtained can then be compared with predicted size of the fusion protein.

Two or more generations of transgenic plants may be grown and either crossed or selfed to allow identification of plants and strains with desired phenotypic characteristics including production of recombinant proteins. It may be desirable to ensure homozygosity of the plants, strains or lines producing recombinant proteins to assure continued inheritance of the recombinant trait. Methods of selecting homozygous plants are well know to those skilled in the art of plant breeding and include recurrent selfing and selection and anther and microspore culture. Homozygous plants may also be obtained by transformation of haploid cells or tissues followed by regeneration of haploid plantlets subsequently converted to diploid plants by any number of known means, (e.g.: treatment with colchicine or other microtubule disrupting agents).

Preparation of Oil Bodies and Their Use As An Affinity Matrix

Similar methods are used for the preparation of oil bodies from seeds of either transgenic or non-transgenic plants. Typically, seeds are thoroughly ground in five volumes of a cold aqueous buffer. A wide variety of buffer compositions may be employed, provided that they do not contain high concentrations of strong organic solvents such as acetone or diethyl ether, as these solvents may disrupt the oil bodies. For small-scale preparations (e.g. 1–1000 g), the solution density of the grinding buffer may be increased with the addition of 0.4–0.6M sucrose, in order to facilitate washing as described below. For larger-scale preparations employing continuous-flow centrifugation equipment or hydrocyclones, the sucrose may be eliminated. The grinding buffer will also typically contain 0.5M NaCl to help remove soluble proteins that are not integrally bound to the oil body surface.

Following grinding, the homogenate is centrifuged resulting in a pellet of particulate and insoluble matter, an aqueous phase containing soluble components of the seed, and a surface layer comprised of oil bodies with their associated proteins. The oil body layer is skimmed from the surface and thoroughly resuspended in one volume of fresh grinding buffer. It is important that aggregates of oil bodies be dissociated as thoroughly as possible in order to ensure efficient removal of contaminants in the subsequent washing steps. The resuspended oil body preparation is layered under a flotation solution of lower density (e.g. water, aqueous buffer) and centrifuged, again, separating oil body and aqueous phases. This washing procedure is typically repeated at least three times, after which the oil bodies are deemed to be sufficiently free of contaminating soluble proteins as determined by gel electrophoresis. The process can be scaled up to handle larger quantities of seed by using methods such as continuous-flow centrifugation as described by Jacks et al., 1990, *JAOCS* 67: 353–361.

For use as an affinity matrix, washed oil bodies are thoroughly mixed with solutions containing the desired target. Interaction between the ligand and target results in the non-covalent association of the target with the oil body. Following centrifugation, the oil bodies and affinity-bound target are separated from the aqueous phase, effectively purifying the target from any contaminants present in the original solution. Repeating the washing step ensures that any remaining contaminants are removed.

Following their attachment to oil bodies, targets may be eluted under conditions determined empirically for each individual ligand-target pair. Treatment of the bound matrix with the appropriate eluent and centrifugation enables recovery of the purified target in the aqueous phase. If the target is a ligand-protein fusion containing a protease recognition site, then it may be treated with the appropriate protease to remove the ligand. The free ligand may then be separated from the target protein by re-application of the oil body affinity matrix or through conventional protein purification methods.

Applications of Oil Body Affinity Matrices

Given that it is possible to engineer oil body affinity matrices for several classes of proteins, multiple uses for oil body based affinity matrices are envisioned. Bacteria, fungi, plants and animals all contain proteins which are able to specifically interact with agents such as ions, metals, nucleic acids, sugars, lipids and other proteins. These agents may be immobilized using oil body technology.

Oil bodies may be marshalled to separate cells of industrial or medical interest from a mixed population of cells. For example haematopoietic stem cells, which are a subpopulation of blood cells and are used in bone marrow transplantations and in stem cell gene therapies, may be separated from other blood cells using oil body based affinity technology. In recombinant DNA technology it is often required that cells in which recombinant DNA has been successfully introduced, known as transformed cells, are distinguished and separated from cells which failed to acquire recombinant DNA. Provided that part of the recombinant DNA expresses a cell surface protein which is complementary to a oil body based affinity ligand, it is possible to utilize oil bodies to separate transformed cells from untransformed cells. Oil body affinity technology may also be used to separate cellular organelles such as chloroplasts and mitochondria from other cellular material.

It is also possible to immobilize a class of proteins known as metalloproteins, which contain prosthetic groups that specifically bind ions. Examples of metalloproteins are haemoglobin, which binds iron, parvalbumin which binds calcium and metallothionein a protein which binds zinc and other metal ions. It is envisioned that oil bodies could be used to scavenge metals from streams of flowing material, which might be water contaminated with the waste of metals from laboratories and industrial processes. Example 4 given below further illustrates this application. Other examples where proteins may be bioimmobilized and employed in a bioremediation strategy include the removal of phosphates, nitrates and phenols from waste streams. In part this approach may overcome the real or perceived limitations of bacterial bioremediation.

In certain instances it may not be practical or necessary to rely on affinity partitioning technology to separate the oil body matrix from the target compound. In these instances, it is envisioned that oil bodies may be immobilized on a solid inert surface which could be a flat surface or the surface of a column. A solution containing the affinity ligand may then be passed over the surface coated with immobilized oil bodies whereupon selective affinity binding occurs. It is envisioned that immobilized oil bodies may be used in pipes and in ponds to assist in bioremediation.

The following examples illustrate various systems in which oil bodies can be used as affinity matrices. It is understood that the examples given below are intended to be illustrative rather than limiting.

EXAMPLE 1

Purification of Thrombin

The following example demonstrates the utility of an oil body affinity matrix for the purification of thrombin. Thrombin is a serine protease which plays a central role in blood coagulation. It cleaves fibrinogen to produce fibrin monomers which polymerize to form the basis of a blood clot (Fenton 1981; *Ann. N.Y. Acad. Sci.* 370: 468–495). Alfa-thrombin consists of two polypeptide chains of 36 (A-chain) and 259 (B-chain) residues linked by a disulphide bridge. Degen et al. 1983; *Biochemistry* 22: 2087–2097). Hirudin, which is found in the salivary glands of the medicinal leech *Hirudo medicinalis,* is a very specific and potent inhibitor of thrombin. This inhibition is a result of the non-covalent binding of hirudin to specific parts of the alfa-thrombin chain. (Stone and Hofsteenge 1986; *Biochemistry* 25: 4622–4628).

The immobilized ligand is comprised of an isoform of hirudin fused to the 18 kD Arabidopsis oleosin (oil body protein) (Van Rooijen et al., 1992; *Plant Mol. Biol.* 18: 1177–1179). Expression of the construct is regulated by the Arabidopsis 18 kD oleosin promoter (Van Rooijen et al., 1994; *Plant Mol. Biol.* 18: 1177–1179). The sequence of the oleosin-hirudin fusion is shown in FIG. 2 and in SEQ.ID.NO:3.

Oleosin-Hirudin Construct

Oligonucleotide primers were designed based upon the reported sequence for a *Brassica napus* oleosin gene (Murphy et al. 1991, *Biochim. Biophys. Acta* 1088: 86–94) and used to amplify a fragment from *B. napus* genomic DNA through PCR. Using this fragment as a probe, a clone carrying a 15 kb insert was identified and isolated from a EMBL3 Arabidopsis genomic library. Oligonucleotide primers were used to amplify a fragment from this insert containing the entire oleosin coding sequence and intron together with 840 basepairs of the 5' upstream region. The primers were designed so as to eliminate the translational stop codon and to introduce a PstI restriction endonuclease recognition site at the 5' end and a SalI followed by a PvuI site at the 3' end of the fragment. The fragment was end-filled and ligated into the SmaI site of the plasmid vector pUC19. A SalI-EcoRI fragment from plasmid pBI121 (Clonetech) comprising the nopaline synthetase terminator sequence was then inserted to generate pOBILT.

A synthetic hirudin variant 2 (HV2) sequence was synthesized based upon reported sequence information (Harvey et al. 1986, *Proc. Natl. Acad. Sci. USA* 83: 1084–1088) but employing *B. napus* and Arabidopsis codon usage. The sequence was amplified using four overlapping oligonucleotide primers designed such that the resulting fragment possessed PvuI and SalI sites at the 5' and 3' ends respectively. This fragment was ligated into the SmaI site of the pUC 19 plasmid vector to generate pHIR. The PvuI-SalI fragment from pHIR was then inserted into pUCOBILT between the oleosin and terminator sequences to form an in-frame fusion with the oleosin coding region giving pUCOBHIRT. The entire construct was subcloned into pBluescript KS+ (pBIOBHIRT) and then into the PstI site of pCGN 1559 plasmid carrying a neomycin phosphotransferase gene under control of the 35-S CaMV promoter (pCGOBHIRT). This plasmid was introduced into *Agrobacterium tumefaciens.* The preparation of this plasmid is shown in FIG. 3.

Transformation and Regeneration

Procedures for the transformation of Agrobacterium and plants have been described previously. *Agrobacterium tumefaciens* were transformed with the above construct through electroporation (Dower et al., 1988; *Nucl. Acids Res.* 16: 6127–6145). These bacteria were then used to transform cotyledonary explants of *Brassica napus,* followed by plant regeneration according to the methods of Moloney et al. (1989; *Plant Cell Reports* 8: 238–242). Transgenic plant were initially identified using a neomycin phosphotransferase assay and subsequently confirmed by expression of the oleosin-hirudin fusion as determined through northern and immunoblot analysis.

Preparation of Oil Bodies

Seed from either control (non-transgenic) plants or transgenic plants expressing the oleosin-hirudin fusion were homogenized in five volumes of cold grinding buffer (50 mM Tris-HCl, pH 7.5, 0.4M sucrose and 0.5M NaCl) using a polytron operating at high-speed. The homogenate was centrifuged at approximately 10×g for 30 min. to remove particulat matter and to separate oil bodies from the aqueous phase containing the bulk of soluble seed protein. Oil bodies were skimmed from the surface of the supernatant with a metal spatula and placed in one volume of fresh grinding buffer. To achieve efficient washing in subsequent steps, it was important to ensure that the oil bodies were thoroughly redispersed. This was accomplished by gently re-homogenising the oil bodies in grinding buffer with the polytron operating at low-speed. Using a syringe, the resuspended oil bodies were carefully layered underneath five volumes of cold 50 mM Tris-HCl, pH 7.5 and centrifuged as above. Following centrifugation, the oil bodies were again removed and the washing procedure repeated three times to remove residual contaminating soluble seed proteins. The final washed oil body preparation was resuspended in one volume of cold 50 mM Tris-HCl pH 7.5, redispersed with the polytron, and was then ready for use as an affinity matrix.

Affinity Purification of Thrombin

Figure 4:
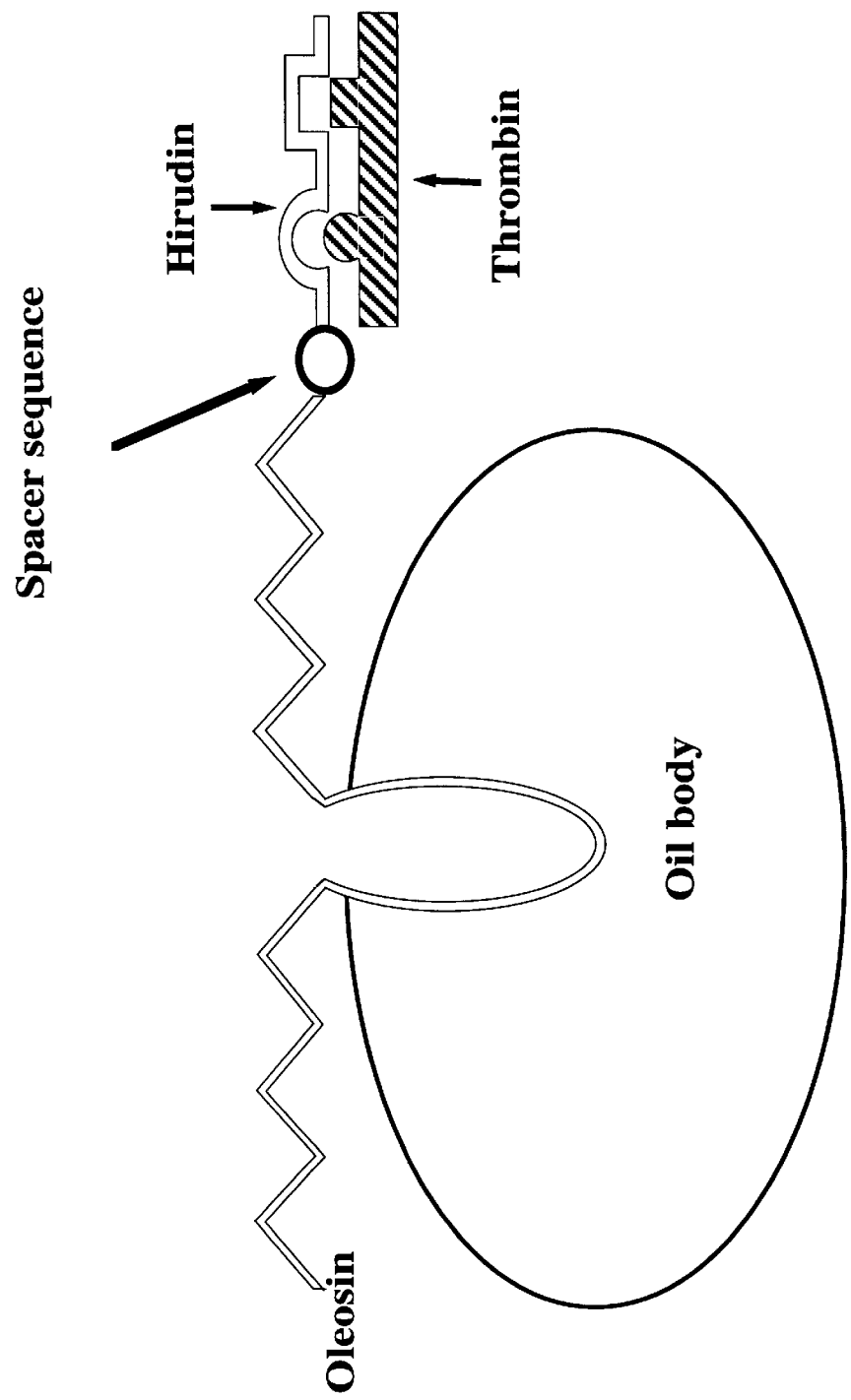
FIG. 4. Schematic diagram illustrating the configuration of the oleosin-hirudin fusion protein on the oil body and the binding of thrombin.

The purification of thrombin using the oleosin-hirudin fusion protein is shown schematically in FIG. 4. In order to evaluate the binding of thrombin, affinity matrices were prepared from transgenic *Brassica napus* seeds expressing the oleosin-hirudin fusion protein (4A4 seeds) (Parmenter et al. *Plant Molecular Biology* (1995) 29: 1167–1180) and from wild type *Brassica napus* cv Westar seeds. Binding of thrombin to both matrices was evaluated. Procedures for the preparation of washed oil bodies from seeds were the same as those described above. Solutions containing a range of thrombin activities between 0 and 1 units were mixed with 10 μl of a fixed amount of affinity matrix (prepared from a total of 10 mg of dried seeds; corresponding to approximately 100 μg of total oil body protein) in 500 μl binding buffer (50 mM Tris-HCl (pH 7.5); 0.1% (w/v) BSA). The oil body suspension was then incubated for 30 minutes on ice and centrifuged at 14,000 rpm for 15 minutes at 4° C. The buffer under the oil bodies ('unternatant') containing the unbound, free thrombin was recovered using an hypodermic needle and assayed for thrombin activity as follows. A total of 250 μl of unternatant was added to 700 μl binding buffer and prewarmed to 37° C. Following the addition of 50 μl of 1 mM thrombin substrate N-p-tosyl-gly-pro-arg-p-nitroanilide (Sigma) to the unternatant, the change in optical density at 405 nanometers was monitored spectrophotometrically for 3 minutes. The concentration of thrombin in the assay mixture was determined employing a standard curve which was constructed using a set of thrombin samples containing known concentrations of thrombin. The values obtained from these assays were used to calculate the concentration bound thrombin assuming:

$$[\text{bound thrombin}] = [\text{total thrombin}] - [\text{free thrombin}]$$

The ratio of the concentration of bound over the concentration of free thrombin was plotted as a function of the concentration of bound thrombin (Scatchard plot). From these plots the dissociation constants of the affinity matrix were calculated following standard procedures (Scatchard, G. Ann. N.Y. Acad. Sci. (1949) 57: 660–672) and assuming: $K_a=1/K_d$. Table 1 shows the recovery of bound thrombin from an oil body-hirudin matrix.

Figure 5:
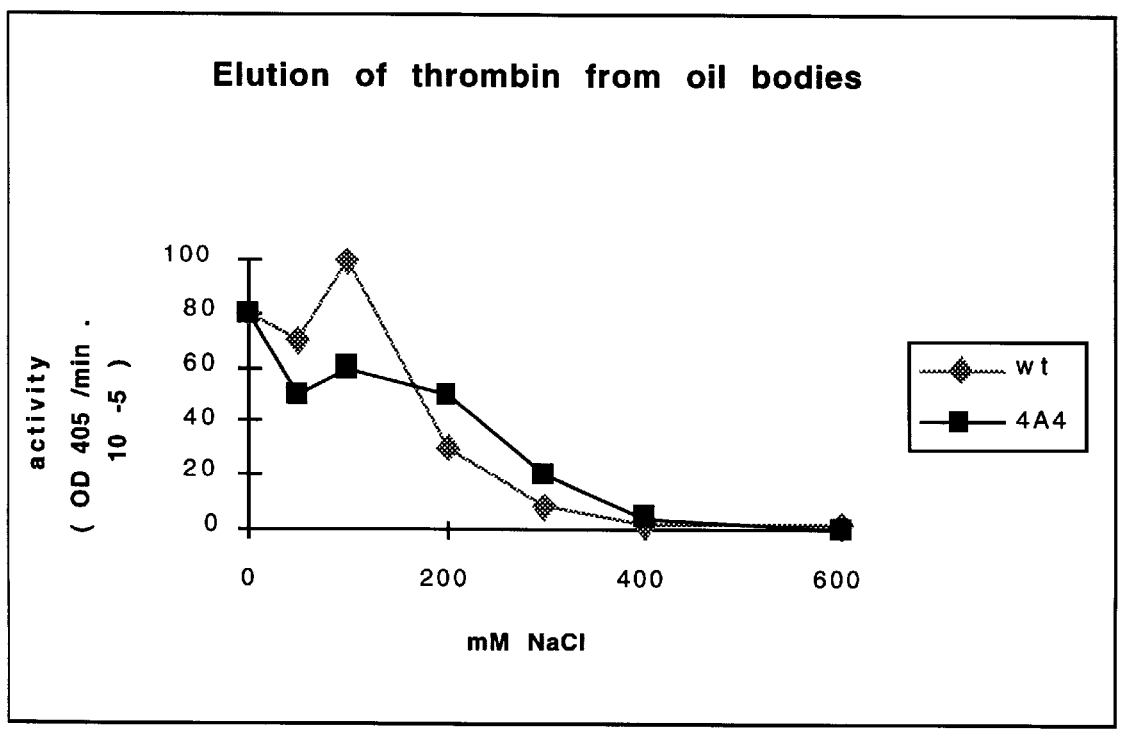
FIG. 5. NaCl elution profiles of thrombin from wild type and 4A4 oil body matrices.

In order to evaluate the recovery of bound thrombin from the matrices a NaCl gradient was employed. The elution profile of thrombin bound to oleosin-hirudin oil body matrices was compared with the profile from thrombin bound to wildtype oil body matrices. Procedures for preparation of wild type oil bodies from wild type Brassica napus cv Westar seeds and for the preparation of oleosin-hirudin oil bodies from Brassica napus 4A4 seeds (Parmenter et al. Plant Molecular Biology (1995) 29: 1167–1180) were identical to those described above. Procedures for binding of thrombin to the matrices were as described above, except 100 μl aliquots of oil bodies were used to bind 0.5 units of thrombin. Oil body suspensions were left on ice for 30 minutes prior to centrifugation for 15 minutes at 4° C. and 14,000 rpm. The unternatant was assayed for (unbound) thrombin activity. The oil body matrix was then resuspended in binding buffer to which NaCl was added to a final concentration of 0.05M. Starting with the 30 minutes incubation of the oil body suspension on ice, the procedure was repeated five times increasing the NaCl concentration in a stepwise fashion. The final NaCl concentrations used were 0.05M, 0.1M, 0.2M, 0.3M, 0.4M and 0.6M. The NaCl concentrations in the thrombin assay were kept constant at 150 mM. FIG. 5 shows the elution profiles obtained when wildtype oil bodies and 4A4 oil bodies were used.

TABLE 1

Dissociation constant ($K_d$) of wild type and 4A4 affinity matrices

|  | Wild Type | 4A4 |
| --- | --- | --- |
| $K_d$ | $3.22 \times 10^{-7}$ M | $2.60 \times 10^{-8}$ M |

EXAMPLE 2

Use of Antibodies as Bivalent Ligands

Figure 6:
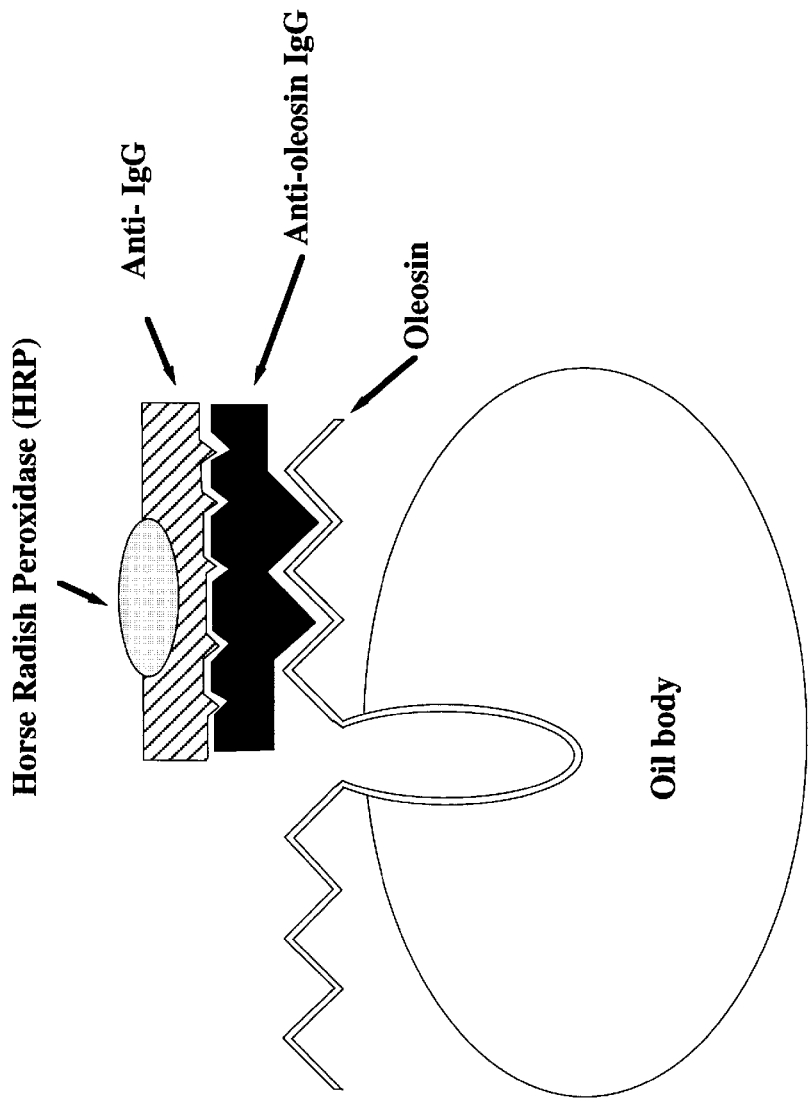
FIG. 6. Purification of a horseradish peroxidase conjugated anti-IgG antibody using an anti-oleosin antibody as a ligand. Schematic diagram illustrating the configuration of the oleosin/anti-oleosin/anti-IgG sandwich complex bound to an oil body.

Antibodies may be used as bivalent ligands by virtue of their affinity both for specific epitopes and for other antibodies or proteins (for example the Staphylococcus aureus protein A) which have affinity for immunoglobulins (IgGs). In this example, polyclonal anti-oleosin antibodies serve as a bivalent ligand and antibodies raised in rabbits against the anti-oleosin antibodies serve as the target. This example is illustrated schematically in FIG. 6.

Figure 7:
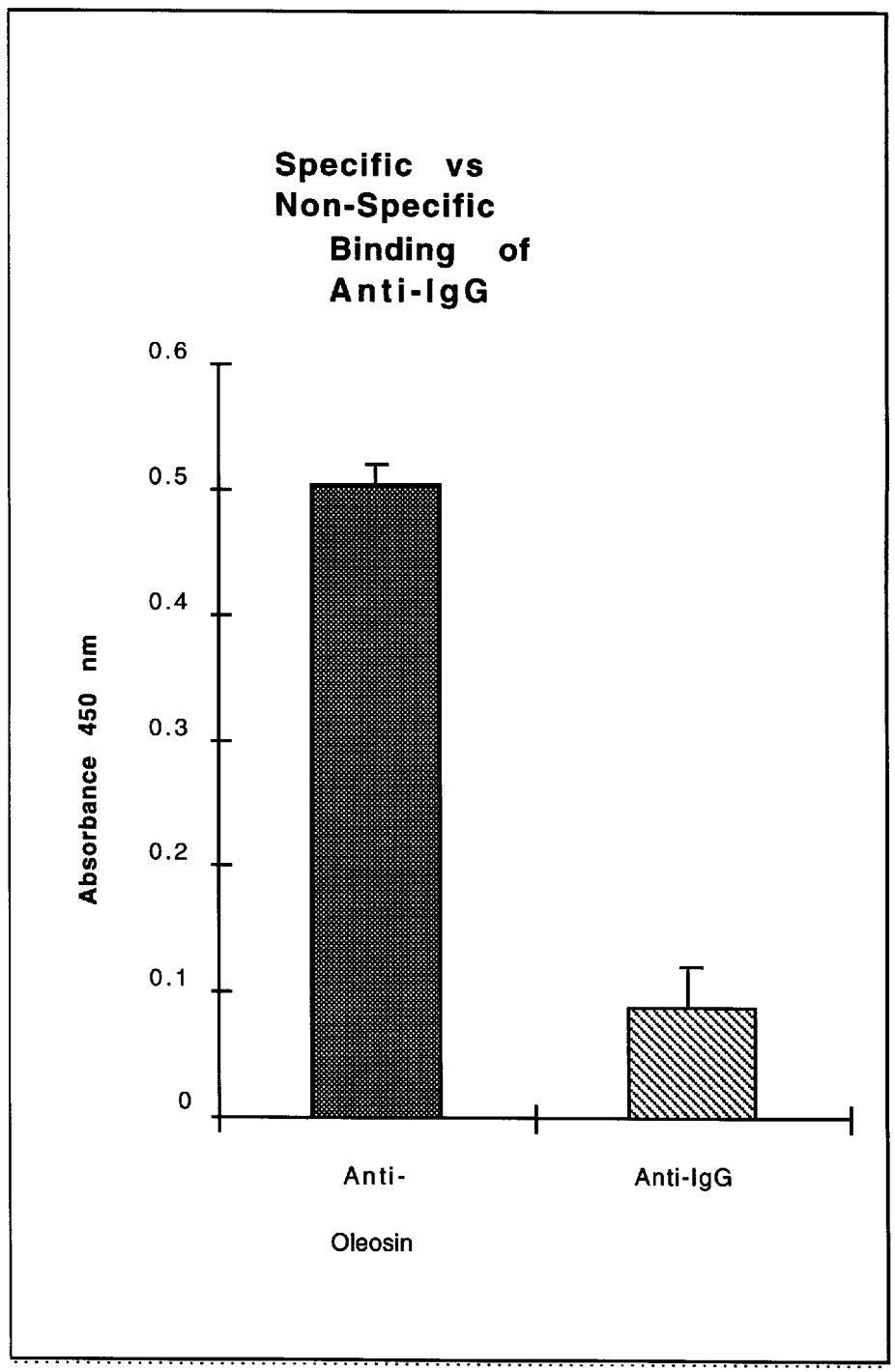
FIG. 7. Illustrates specific binding of anti-IgG antibodies to wild type oil bodies complexed with primary anti-oleosin antibodies as a ligand (left) and binding of anti-IgG antibodies to oil bodies which were not complexed with primary antibodies prior to binding with the secondary antibodies (right).

Oil bodies were prepared from 5 g of wild type Brassica napus cv Westar seeds following the procedure described in Example 1. Subsequently, oil bodies were washed twice with 100 mM glycine (pH 2.5), neutralized through two washes in binding buffer (50 mM Tris-HCl, pH 7.5) and resuspended in 5 ml of binding buffer. A 150 μl aliquot of the washed oil body preparation was combined with 500 μl of rabbit serum containing anti-oleosin antibodies (ligand antibodies), diluted 1:10 with binding buffer. The oil body suspension was mixed thoroughly and incubated for 1 h at 4° C. with agitation. Following incubation, unbound ligand antibodies were removed from the oil body suspension through three washes with 1 ml of binding buffer. Oil bodies were then combined with 500 μl of serum diluted 1:500 in binding buffer and containing anti-rabbit IgG antibodies (the target antibodies) conjugated with horseradish peroxidase (HRP) as a detection label (Sigma). This suspension was mixed and incubated under conditions identical to those used for the anti-oleosin antibody binding. As a control, target antibodies were incubated with oil bodies which had not been previously bound to ligand antibodies. Both samples were subsequently washed four times with 1 ml of binding buffer to remove unbound antibodies. Using binding buffer, the samples were equalized with respect to concentration of oil bodies as determined by measuring sample turbidity spectophotometrically at 600 nm. To assay for bound target antibody, samples containing 5 μl of oil bodies were mixed with 1 ml of the HRP colorimetric substrate tetramethylbenzidine in 0.01% hydrogen peroxide and reacted for 10 minutes at room temperature. Reactions were stopped by the addition of 500 μl of 1M $H_2SO_4$ and the absorbance at 450 nm was determined. Corrections for the presence of residual, unbound target antibody remaining after washing were made by assaying 5 μl of the final wash fraction. The results obtained for control and ligand bound oil body preparations are set forth in FIG. 7.

EXAMPLE 3

Use of Oleosin-Specific Ligands

The use of an oleosin-specific ligand represents an alternative to the use of an antibody or genetically-engineered oleosin fusion proteins for the purification of recombinant target proteins. In this case, the target protein is fused to the oleosin-specific ligand and the endogenous oleosins present on the oil bodies of non-transgenic seeds serve as the complementary ligand-affinity matrix. In addition to eliminating the requirement for a transgenic line expressing an oleosin fusion, this approach increases the overall capacity of the affinity matrix, since all of the endogenous oleosins may now participate in binding.

Oleosin-specific ligands may be identified and isolated from a peptide phage display library screened with oleosin protein. Since the extreme hydrophobicity of the oleosin central domain can result in aggregation and precipitation of the protein when removed from oil bodies, a mutant protein lacking this domain may be used for screening. This has little effect on the efficacy of the ligand, as only the hydrophillic portions of the oleosin are exposed to the cytoplasm (i.e. the N- and C-termini). Hence, these are the only regions available for binding to a ligand. Once isolated, the ligand may be fused to a common reporter protein, green fluorescent protein (GFP) (Prasher, 1995, Trends Genet. 11:320–323), to demonstrate purification.

Removal of the Oleosin Central Domain

Oligonucleotide primers specific for the Arabidopsis oleosin gene described above can be used to amplify an oleosin gene from a B. napus cDNA library (van Rooijen 1993, Ph.D. Thesis, University of Calgary). Primers flanking sequences encoding the N-terminal 62 amino acids and the C-terminal 55 amino acids, may be used to amplify sequences for the respective N- and C-terminal oleosin domains in separate reactions. Additionally, the primer for the 5' end of the N-terminal domain contains a sequence for a thrombin recognition site to enable cleavage of the fusion protein as described below. The resulting fragment was ligated into the SmaI site of the bacterial expression vector pEZZ 18 (Pharmacia). This vector contains sequences encoding a signal peptide for protein secretion into the periplasm, and synthetic IgG binding domains derived from protein A to facilitate protein purification, downstream of the multiple cloning site.

Expression and Purification of the Oleosin Deletion Construct

The vector carrying the deletion mutant construct is introduced into *E. coli* using standard methods and transformants selected. A culture of the transformed bacteria can be induced to express the synthetic protein A-mutant oleosin fusion protein by addition of 1 mM IPTG. Induced cells may be pelleted and resuspended in 5 mM $MgSO_4$ causing lysis of the periplasmic membrane through osmotic shock. The lysed cells are centrifuged and the supernatant containing the secreted protein is loaded on to a column containing IgG-coupled sepharose. After washing to remove unbound protein, the column is loaded with a buffer containing 50 mM Tris-HCl, pH 7.5, 150 mM NaCl and 1.0 U/ml of purified Bovine thrombin (Sigma) to cleave the mutant oleosin from the synthetic protein A. Following incubation at 37° C. for 4 h, the column is drained and the eluate passed through a column of heparin-coupled sepharose to remove thrombin. The eluate from this column, containing the mutant oleosin protein, is recovered and purity of the protein examined through gel electrophoresis followed by staining with Coomassie blue R250.

Generation of a Peptide Combinatorial Library

A random peptide combinatorial library may be generated according to the methods of Scott and Smith (1990; *Science* 249: 386–390). Briefly, the PCR is used to amplify a synthetic DNA fragment containing the degenerate sequence $(NNK)_6$; where 'N' represents an equal mixture of deoxynucleotides G, A, T, and C, and K represents an equal mixture of deoxynucleotides G and T. The degenerate sequence encodes for hexameric peptides among which are represented every possible combination of the 20 amino acids and amber stop codon. The PCR product is ligated into the gene III sequence of the filamentous bacteriophage fUSE and the resulting phagemid introduced into *E. coli* through electroporation.

Identification and Isolation of Oleosin-Specific Ligands

The peptide phage display libraries are amplified, concentrated and stored in aliquots of $10^{12}$ tdu/ml. Purified mutant oleosin protein is biotinylated using a thiol-cleavable linker (S-S biotin, Pierce) and purified by size exclusion chromatography. Aliquots of the peptide phage display library containing $5 \times 10^{11}$ tdu in two ml are screened with the biotinylated protein at a concentration of 50 nM. Phage binding the mutant oleosin protein are recovered using streptavidin-coated paramagnetic beads. Following washing, the phage are eluted through the addition of 50 mM dithiothreitol which cleaves the disulphide bond. The eluted phage are then incubated with an excess of log-phase F+ *E. coli*. Aliquots of the infected cells are plated to determine the phage titre and the remaining cells used in successive rounds of amplification and screening. Following enrichment of the eluted phage by 3–4 orders of magnitude, individual phage are selected and tested for binding to mutant oleosin by direct ELISA. Binding by phage is detected using anti-phage antibodies (Crosby and Schorr, 1995, In *Annual Review of Cell Biology*). Single stranded DNA is isolated from phage exhibiting binding and the peptide-encoding sequence determined.

Affinity Purification with Oleosin-Specific Ligands

The sequence for an oleosin ligand isolated as described above is fused in-frame upstream the sequence for gfp10 (Prasher et al., 1992, *Gene* 111: 229–233) encoding GFP and the construct ligated into the bacterial expression vector pKK233 (Pharmacia). Soluble protein is extracted through sonication of cells induced to express the ligand-GFP fusion, and adjusted to a concentration of 10 mg/ml in 50 mM Tris-HCl, pH 7.5.

Twenty ml of the protein solution is mixed with 2 ml of oil bodies prepared as described above, from seeds of non-transgenic plants. The mixture is incubated at 4° C. for 30 min with agitation to allow binding and then centrifuged to separate the oil bodies and soluble fraction. The amount of GFP remaining in the soluble fraction after removal of oil bodies is determined by fluorescence spectrofluorometry at a wavelength of 508 nm and compared with that in the original bacterial extract. The amount of bound GFP is calculated to determine the capacity of the matrix.

The oil bodies are washed twice in 20 ml of 50 mM Tris-HCl, pH 7.5, resuspended in 2 ml of the same buffer and divided into 20 aliquots of 100 µl. Conditions for the elution of ligand-GFP fusion protein are determined by adding 1 ml of solutions ranging in pH from 2–10 and in NaCl concentration from 0–1M to different aliquots. After mixing and incubation at 4° C. for 30 min, the oil bodies are removed and the soluble fractions collected. The amount of ligand-GFP fusion protein in the soluble fraction is determined by fluorescence spectrophotometry.

EXAMPLE 4

Removal of Heavy Metal Ions

The following example demonstrates the utility of oil body affinity matrices for the recovery/removal of non-protein targets from complex solutions. For the purpose of this example the metallothionein/$Cd^{++}$ ligand pair was used. However other metal binding proteins such as phytochelatins (Rauser, 1990; *Ann. Rev. Biochem;* 59: 61–86) and metal ions including $Cu^{++}$ and $Zn^{++}$ could also be used.

Oleosin-Metallothionein Fusion

Figure 9:
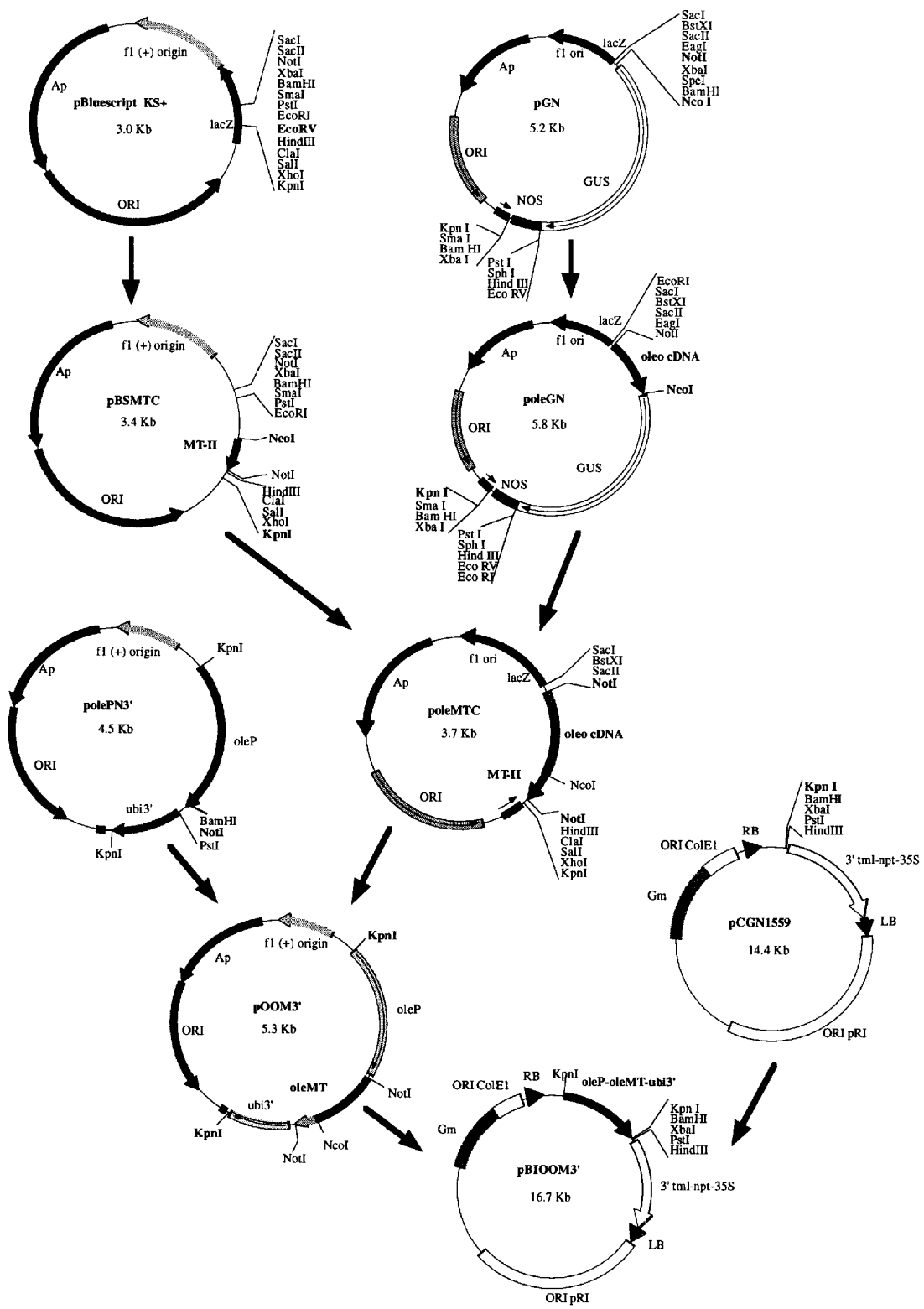
FIG. 9. Outline of the steps employed in the construction of pBIOOM3' containing the entire oleosin-metallothionein construct.

An oleosin gene from a *B. napus* cDNA library (van Rooijen 1993, Ph.D. Thesis, University of Calgary) was amplified through PCR with oligonucleotide primers designed so as to create NotI and NcoI sites at the 5' and 3' ends of the gene respectively. The resulting fragment was digested and placed into the NotI/NcoI sites of pGN to yield plasmid poleGN. The human metallothionein gene, mt-II (Varshney and Gedamu, 1984, *Gene,* 31: 135–145) was amplified using oligonucleotide primers designed to create a unique NotI site at the 3'-end of the gene. The resulting PCR product was subcloned into the blunt-end EcoRV site of pBluescript KS+ to form pBSMTC. The mt-II gene was then excised from this plasmid and subcloned into the NcoI/KpnI sites of poleGN replacing the GUS-NOS region to generate pOLEMTC. The 773 base oleosin-MT fusion of pOLEMTC was excised with NotI digestion and inserted into the unique NotI site of polePN3' between the oleosin promoter (oleP; Van Rooijen et al., 1992, *Plant Mol. Biol.* 18: 1177–1179) and the *P. crispum* ubi4-2 gene terminator (ubi3'; Kawalleck et al., 1993, *Plant Mol. Biol.* 21: 673–684.) to generate pOOM3'. After the fusion was determined to be in the correct orientation, pOOM3' was digested with KpnI to release the oleP-oleMT-ubi3' insert. This expression cassette was inserted at the KpnI site of the binary vector pCGN1559 to yield the final construct pBIOOM3'. The sequence of the oleosin-metallothionein fusion is shown in FIG. 8 and SEQ.ID.NO.6. The plasmid pB100M3' is shown in FIG. 9.

Transformation and Regeneration

Transgenic plants expressing the oleosin-metallothionein fusion were created as described in Example 1.

Oil Body Preparation

Washed oil bodies may be prepared from seeds of transgenic and control plants as described in Example 1.

Removal of Cd++ From Solution Using an Oil Body Affinity Matrix

Figure 10:
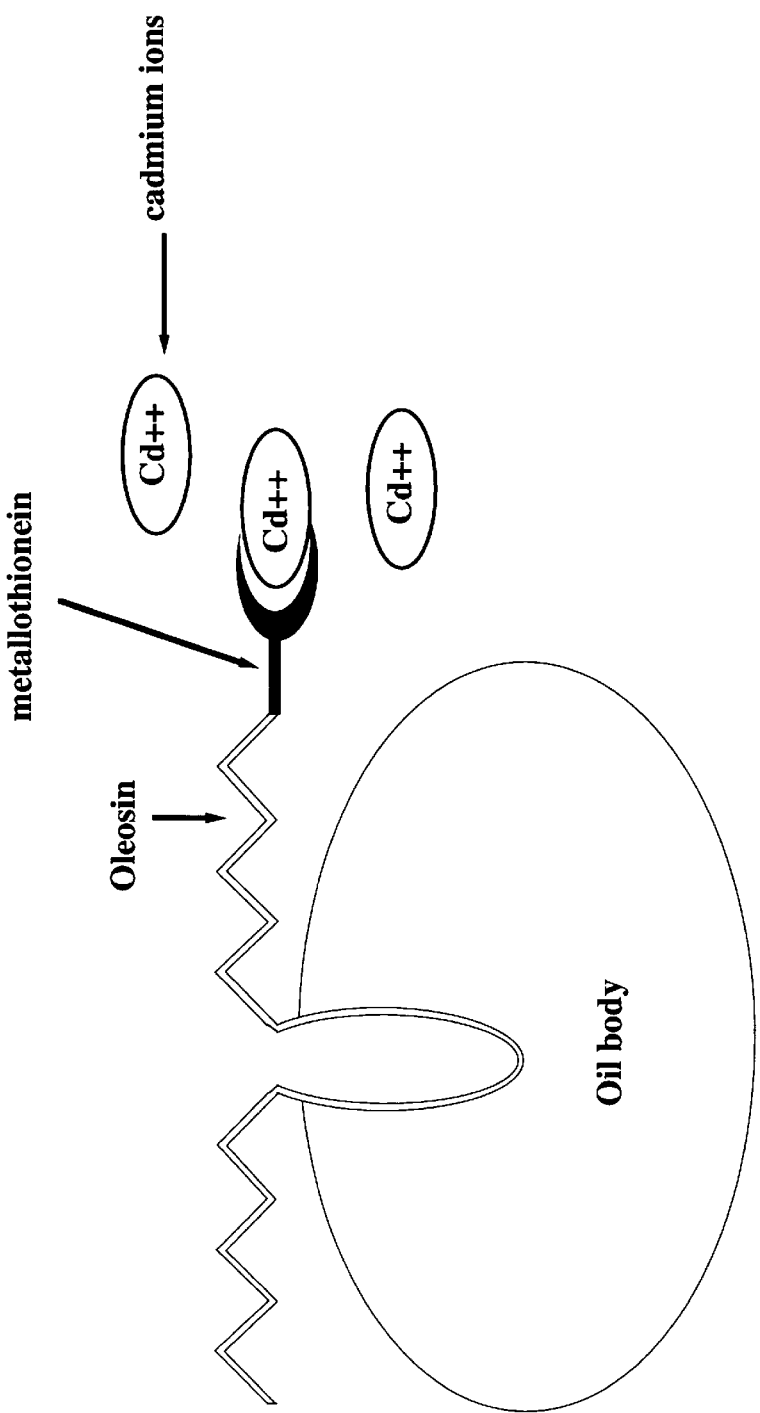
FIG. 10. Schematic diagram illustrating the configuration of the oleosin-metallothionein fusion protein on the oil body and binding of cadmium ions.

The use of the oleosin-metallothionein fusion to bind cadmium ions in solution is shown schematically in FIG. 10.

Solutions ranging in concentration from 1 µM to 1 mM, are prepared from a 1 mM solution of $CdCl_2$ in 50 mM Tris-HCl, pH 7.5 containing 10 nM $^{109}Cd$. One ml aliquots of these solutions are thoroughly mixed with 100 µl of washed oil bodies prepared from seeds expressing the oleosin-metallothionein fusion protein and incubated at 22° C. for 30 min. Following centrifugation to separate the oil bodies, the amount of $^{109}Cd$ remaining in the aqueous phase is determined through scintillation counting and the values used to calculate the capacity of the affinity matrix. An identical experiment is performed with oil bodies from non-transgenic seeds to detect and correct for non-specific binding.

If desired the $Cd^{++}$ ions can be released from the oil body metallothionein affinity matrix at this point by treatment with a low pH buffer (pH <3.0) (Pazirandeh et al., 1995; Appl. Microbiol. Biotechn. 43: 1112–1117). The matrix may be used for subsequent rounds of cadmium ion removal.

EXAMPLE 5

Separation of Whole Cells

The following example illustrates the capacity of oil bodies to immobilize whole cells. One potential for the use of bacterial cell separation lies in the utility for diagnostics. It is also desirable to separate unique eukaryotic cells such as lymphocytes and stem cells from complex mixtures of cells where the cell type of interest is present in relatively low numbers.

Differential Binding of Two Strains of Staphylococcus aureus

In this experiment an oil body affinity matrix is employed to demonstrate differential binding of two strains of Staphylococcus aureus. Formalin fixed S. aureus strains, one expressing the IgG binding surface antigen protein A and one lacking protein A, are commercially available from Sigma. Dilute aliquots of both S. aureus strains of equal $OD_{550}$ could be prepared. To each of these aliquots control oil bodies from untransformed plants or oil bodies mixed with anti-oleosin antibodies could be added. Following incubation for an appropriate length of time at an appropriate temperature, the samples could be centrifuged to pellet unbound bacterial cells and to separate the oil body fraction. The oil bodies could be decanted, vortexed and the $OD_{550}$ could be determined. The pellets could be resuspended and the $OD_{550}$ of the unternatant could be determined. It is anticipated that only in the sample containing the S. aureus strain expressing protein A and the oil body complexed with anti-oleosin antibodies, fractionation of these cells to the oil body fraction will be observed. Binding of the cells to the oil body could be further demonstrated by lowering of the pH of the oil body fraction. Subsequent to centrifugation the release of cells from the oil bodies could be evidenced by the presence of a pellet and/or an increase in $OD_{550}$ upon resuspension of the pellet.

Separation of Staphylococcus aureus from E. coli

A viable S. aureus strain could be mixed with varying quantities of cells of an E. coli strain having a specific antibiotic resistance. The mixed bacterial sample could be vortexed with control antibodies and with oil bodies which have been complexed with anti-oleosin antibodies. After incubation for an appropriate length of time and at an appropriate temperature oil bodies could be washed and the unternatant and oil bodies could be directly titrated and selectively plated on blood agar for S. aureus growth and on LB plates for E. coli growth. The enrichment or actual separation obtained could be determine by an estimate of colony forming units.

Identification of Pathogens Present in Low Concentrations in a Complex Mixture

For diagnostic purposes it is often desirable to concentrate bacterial or viral pathogens which invade human or animal tissues in low numbers. An oil body affinity matrix could be used to enrich for these pathogens, so that they could subsequently be identified and characterized.

Pathogens often specifically bind to human or animal cells through the interaction with a receptor or surface protein. Oleosin could be fused to the human or animal protein ligand and recombinant oil bodies could be employed to immobilize the pathogens. Examples of the formation of protein complexes formed between proteins of human and pathogenic origins known to the prior art include: human fibrinogen or fibrin specific domains which bind to S. aureus protein clumping factor A (clf-A) (McDevitt et al. 1995; Mol. Microbiol. 16; 895–907); human decay accelerating factor (DAF) to which urinary and intestinal tract pathogenic E. coli bind (Nowicki et al. 1993: J. Of Experim. Med. 178: 2115–2121); a human cell ligand which is expressed in the carcinoma cell line Caco-2 and which binds uniquely to the 28 kD Klebsiella pneumoniae fimbria protein KPF-28 (Di Maretino et al., 1996; Infect. and Immun. 64: 2263–2266) and human cell extracellular matrix fibronectin specific domains which complex specifically with Streptococcus pyrogenes adhesin (protein F) (Ozeri et al., 1996; EMBO J. 15: 989–998).

EXAMPLE 6

Separation of Small Organic Molecules

This example describes how an oil body affinity matrix may be used for the recovery/removal of small organic molecules from solution. By way of example, the small organic molecule, biotin, is purified using avidin as a ligand.

Construction of Avidin Ligands

Avidin is a protein synthesized by avian species and exhibits an extremely high affinity for biotin, a natural co-factor for many carboxylases. Preparations of purified avidin (commercially available from Sigma) can be conjugated chemically to anti-oleosin antibodies using standard procedures known to those skilled in the art. This approach would yield a bivalent avidin ligand suitable to demonstrate affinity-based removal of biotin. Alternatively, an oleosin-avidin gene fusion may be utilized. The gene encoding avidin in chicken (Gallus gallus) has been identified and its sequence has been determined (Beattie et al., 1987, Nucl Acids Res. 15: 3595–3606). Based on the sequence the gene for avidin could be synthesized chemically or through the PCR and fused to the B. napus oleosin (van Rooijen, 1993, Ph.D. Thesis, University of Calgary) as described in example 4. Streptavidin, an analogous bacterial biotin binding protein, could also be employed.

Oil Body Preparation

Washed oil bodies would be prepared from seeds of transgenic plants and/or control plants as described in example 1.

Binding of Bivalent Avidin-Oleosin Ligand

Binding of anti-oleosin antibodies and removal of unbound ligand will be as detailed in example 3.

Removal of Biotin from Solution

Solutions containing known concentrations of biotin could be combined with a fixed amount of oil bodies complexed with an anti-oleosin antibodies conjugated with avidin. Following binding, the mixture would be centrifuged to separate oil body and aqueous fraction. The amount of biotin remaining in the aqueous fraction is determined by competitive ELISA using anti-biotin antibodies conjugated to horse radish peroxidase (HRP). The amount of bound biotin may be calculated assuming:

[bound biotin]=[total biotin]-[free biotin]

From the obtained values, the dissociation constants can be determined as described in example 2. As a control, an identical experiment could be performed with oil bodies bound to anti-oleosin antibodies which have not been conjugated with avidin. If desired, biotin could be released from the oil body-avidin matrix through competitive elution using an excess of 2-(4'-hydroxybenzene) benzoic acid (HABA). Elution may also aided by employing a genetically engineered mutant of avidin which exhibits a lower affinity for biotin. Such mutants have been described for the analogous biotin binding protein from bacteria, streptavidin (Chilkoti et al., 1995; *Bio/Technol.* 13: 1198–1204).

EXAMPLE 7

Separation of Carbohydrates

The following example describes the utility of oil body matrices for the recovery of carbohydrates from complex biological mixtures. In this example the inventors demonstrate that an oil body immobilized cellulase is capable of binding cellulose.

Oleosin-Cellulose Binding Domain Fusion

Several of the cellulases produced by the bacterium *Cellulomonas fimi* contain discrete cellulose binding domains (CBDs). These CBDs independantly bind to cellulose even when they are separated by proteolytic cleavage or genetic manipulation from the catalytic domain of the enzyme. Plasmid pUC18-CBDPT contains a fragment coding for the CBD of the beta-1,4-glucanase (Gilkes et al., 1992, *Journal of Biol. Chem.* 267: 6743–6749) and could be used to construct an oleosin-CBD gene fusion. A DNA fragment encoding the CBD domain could be isolated from pUC18-CBDPT using appropriate restriction enzymes or using the PCR. Alternatively, the CBDs of other cellulases from *C. Fimi* or cellulases from other sources could be used. An oleosin gene from *B. Napus* isolated from a cDNA library (van Rooijen, 1993, Ph.D. Thesis, University of Calgary) was cloned in pGN using the PCR and yielding plasmid pOLEGN as described in example 4. An in-frame gene fusion between the oleosin gene and the CBD gene could be generated using standard molecular techniques known to those skilled in the art. The final construct would comprise the CBD domain translationally fused immediately downstream of the oleosin.

Transformation and Regeneration

In order to introduce the fusion gene construct in plants, it would be subcloned in a binary vector, such as pCGN1559. Transgenic plants which express the oleosin-CBD fusion could be generated as described in example 1.

Oil Body Preparation

Washed oil bodies could be prepared from the seeds of transgenic and control wild type plants as described in example 1.

Removal of Cellulose from Solution Using an Oil Body Affinity Matrix

In order to evaluate binding of cellulose to the oil body affinity matrix, the binding capacities of oil bodies of wild type and transgenic plants are compared. Oil bodies could be mixed with appropriately buffered solutions containing a range of cellulose concentrations. The oil body suspension could then be incubated for an appropriate length of time and at an appropriate temperature. Upon centrifugation, the unternatant could be recovered and assayed for cellulose concentrations. The concentrations bound cellulose and free cellulose could be calculated assuming:

[bound cellulose]=[total cellulose]-[free cellulose]

The ratio of the concentration bound over the concentration free cellulose could be plotted as a function of the concentration of bound cellulose. From these plots dissociation constants could be calculated following standard procedures (Scatchard, G. *Ann. N.Y. Acad. Sci.* (1949) 57: 660–672) and as detailed in example 2.

EXAMPLE 8

Separation of Nucleic Acids

The following example describes a method in which oil bodies are employed to bind single stranded (SS) nucleic acids.

Isolation of Single Stranded Nucleic Acids

A method for capturing SS nucleic acids may be used in diagnostics, such as plant viral disease, or in research applications where non-reannealed SS nucleic acids need to be selectively removed from solutions such as in hybridization reactions for differential screening of expressed genes. Oleosins could be fused with SS DNA or RNA binding proteins or specific domains thereof and could be used to trap SS nucleic acids for identification or further amplification. Well characterized SS nucleic acid binding proteins include: Agrobacterial Ti plasmid Vir E2 protein (Zupan et al., 1995, *Plant Physiol.* 107: 1041–1047); Tobacco Mosaic Virus (TMV) movement protein P30 (Citovsky et al., 1990; *Cell* 60: 637–647; Waigmann et al., 1994 *Proc Natl. Acad. Sci (USA)* 91: 1433–1437); Cauliflower Mosaic Virus coat protein (Thompson et al., 1993; *J. Gen. Virol* 74: 1141–1148) and *E. coli* RecA and single stranded binding (SSB) proteins (Radding, 1991 *J. Biol. Chem.* 266: 5355–5358).

EXAMPLE 9

Separation of Recombinant Proteins

The following example demonstrates the utility of an oil body affinity matrix for the purification of recombinant target proteins. For the purposes of this example, the IgG/protein A ligand pair has been chosen. Two genetic constructs were employed. One construct consists of an IgG domain which has been fused to the target protein, green fluorescent protein (GFP). The second construct consists of a protein A domain which has been fused to the 18 kDa Arabidopsis oleosin (Van Rooijen et al., 1994; *Plant Mol. Biol.* 18: 1177–1179). The oleosin-protein A fusion protein has been introduced in plants, while expression of the IgG-GFP construct could be in *E. coli.*

The Oleosin-Protein A fusion

A synthetic protein A sequence encoding a protein capable of binding to IgG was synthesized based on reported sequence information (pRIT2T, protein A gene fusion vector; Pharmacia) and was amplified through the PCR. Each primer used in the PCR contained unique restriction sites 5' to the protein A-specific sequence in order to facilitate cloning. The reverse primer (i.e. The primer in the antisense direction) also contained a translational stop codon following the cosing sequence. The resulting fragment was ligated into a pUC19 plasmid carrying the Arabidopsis oleosin gene comprised of an 800 bp upstream promoter region followed by the coding region (with its associated intron) from which the translational stop codon had been removed. The 3' end of the construct contains the nopaline synthase transcriptional terminator. Ligation was performed in such a fashion that the fragment inserted between the oleosin and terminator sequences and an in-frame fusion C-terminal fusion with the oleosin coding region was formed. The entire construct (FIG. 11 and SEQ.ID.NO:8) was then excised from the pUC19 plasmid and subcloned into pCGN1559 carrying a neomycin phosphotransferase gene under the control of the 35S CaMV promoter. The resulting plasmid was introduced in Agrobacterium.

The IgG-GFP Fusion

A synthetic IgG Fc-hinge domain sequence encoding a peptide capable of binding protein A could be synthesized based on reported sequence information (Huck et al., 1986; *FEBS Lett.* 208: 221–230) and amplified using the PCR. As described above for the synthetic protein A sequence, primers each would contain suitable restriction sites. However in this case, the reverse primer would lack the translational termination codon and contains instead a sequence encoding the four amino acid recognition sequence for Factor Xa (IEGR) at its 5' end (FIG. 12 and SEQ.ID.NO:12). A series of ligations and subcloning steps could be undertaken to create the final construct which in 5' to 3' direction would contain the synthetic IgG Fc-hinge domain/Factor Xa cleavage site fused in frame to the sequence to the sequence for gfp10 (Prasher et al., 1992, *Gene* 111: 229–233), encoding green fluorescent protein (GFP). The final construct could be ligated in an *E. coli* expression vector such as pKK233 (Pharmacia).

Transformation and Regeneration

Plants were transformed and regenerated as described in example 1. Transgenic plants would initially be identified using a neomycin phosphtransferase assay and subsequently be confirmed by expression of either protein A fusions through Northern and/or immuno blot analysis.

Preparation of Oil Bodies

Oil bodies from the transgenic plant line expressing the oleosin-protein A fusion could be prepared following the procedure described in example 1.

Recovery of Affinity Tagged GFP

Soluble protein could be expressed from *E. coli* expressing the IgG-GFP fusion using sonication and the concentration could be adjusted to 10 mg/ml in 50 mM Tris-HCl, pH 7.5. An appropriate amount of oil bodies prepared from transgenic seeds and containing the oleosin-protein A fusions could be mixed with an appropriate amount of the GFP solution. Following incubation for an appropriate length of time and at an appropriate temperature, the emulsion could be centrifuged to separate the aqueous phase from the oil body phase and the aqueous phase could be assayed again for GFP activity by fluorescence spectrofluorometry at 508 nm. As a control, instead of using oil bodies containing oleosin-protein A fusions, native oil bodies could be used. If significant amounts of GFP activity remains in the aqueous phase following the partioning step, fresh oil bodies could be added and the process could be repeated until most of the activity has been removed. The oil body fraction could then be washed with an appropriate number of volumes of cold water to remove residual, non specifically complexed protein. The aqueous fractions could be assayed for GFP activity to monitor for lost activity due to these washing steps.

To elute GFP, the oil bodies may be mixed with five volumes of cold 100 mM glycine, pH 2.5 and centrifuged. The aqueous phase containing the purified IgG-GFP fusion protein could be assayed and concentrated through ultrafiltration. If desired, the IgG-affinity tag may be cleaved from GFP using Factor Xa at a concentration of 1U/50 µg of protein. GFP could then be further purified using the oleosin-protein A oil body affinity matrix to remove the IgG affinity tag, followed by ion exchange chromatography to remove Factor Xa.

While the above examples relate to specific embodiments of the invention, one skilled in the art will realize that the oil body system herein described can be used to recover an infinite number of target molecules. The method conditions (such as mixing, and incubation times and temperatures) can be altered depending on the targets and ligands used. Further, while the examples describe using a ligand molecule that associates with both the oil body protein and the target, the inclusion of a ligand molecule is not necessary where the target has direct affinity for the oil body protein. The oil body protein can be an oleosin derived from any plant. In addition, an oil body protein analogous to plant oleosins may also be used. For example, a system functionally equivalent to plant oleosins and oil bodies has been described in bacteria (Pieper-Furst et al. 1994, *J. Bacteriol.* 176: 4328–4337). Other systems may be identified in fungi, insects or animals. All such analogous systems are included within the scope of the invention.

All publications, patents and patent applications are herein incorporated by reference in their entirety to the same extent as if each individual publication, patent or patent application was specifically and individually indicated to be incorporated by reference in its entirety.

We claim:

1. A method for the separation of a target molecule from a mixture comprising:
   1) mixing (i) oil bodies that contain a sufficient portion of an oleosin molecule that can associate with the target molecule with (ii) a mixture containing the target molecule to allow the target molecule to associate with the oil bodies; and
   2) separating the oil bodies associated with the target molecule from the mixture.

2. The method according to claim 1 wherein said oleosin associates with said target molecule through a ligand molecule that binds the target molecule.

3. The method according to claim 2 wherein said ligand is a protein that binds an oleosin.

4. The method according to claim 2 wherein said ligand is an antibody that binds to said oleosin.

5. The method according to claim 4 wherein the target is a cell or cell fragment capable of binding the ligand antibody.

6. The method according to claim 5 wherein said cell is *Staphylococcus aureus*.

7. The method according to claim 2 wherein said ligand is a bivalent antibody that binds to both the oleosin and the target molecule.

8. The method according to claim 2 wherein said oleosin is genetically fused to the ligand molecule.

9. The method according to claim 8 wherein said ligand molecule is a cellulose binding protein and said target is cellulose.

10. The method according to claim 8 wherein said ligand molecule is a nucleic acid binding protein and said target is a nucleic acid.

11. The method according to claim 10 wherein said ligand is a single stranded DNA binding protein or an RNA binding protein and said target is a single stranded nucleic acid molecule.

12. The method according to claim 8 wherein said ligand is protein A and said target is an antibody.

13. The method according to claim 8 wherein said ligand molecule is hirudin and the target molecule is thrombin.

14. The method according to claim 13 wherein the hirudin-oleosin fusion is encoded by the DNA sequence shown in SEQ.ID.NO:3.

15. The method according to claim 8 wherein said ligand molecule is metallothionein and said target is cadmium.

16. The method according to claim 15 wherein said metallothionein oleosin fusion protein is encoded by the DNA sequence shown in SEQ.ID.NO:6.

17. The method according to claim 1 wherein said oleosin associates with said target molecule through a first ligand that binds the oleosin conjugated to a second ligand capable of binding the target.

18. The method according to claim 17 wherein said first ligand is an antibody and said second ligand is avidin and said target is biotin.

19. The method according to claim 1 wherein the oleosin is derived from the plant *Arabidopsis thaliana*.

20. The method according to claim 19 wherein the oleosin has the sequence shown in SEQ.ID.NO:1.

21. The method according to claim 1 wherein said target is selected from the group consisting of proteins, peptides, organic molecules, lipids, carbohydrates, nucleic acids, cells, cell fragments and metals.

22. The method according to claim 1 wherein after mixing in step 1), the oil bodies and mixture are incubated for about 15 minutes to about 2 hours.

23. The method according to claim 22 wherein the oil bodies and mixture are incubated for about 30 minutes at 4° C.

24. The method according to claim 1 wherein the oil bodies associated with the target molecule are separated from the mixture by centrifugation, floatation or size exclusion.

25. The method according to claim 1, further comprising 3) separating the target molecule from the oil bodies by elution under appropriate conditions.

* * * * *

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
    ( A ) LENGTH: 522 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Oleosin From Arabidopsis Thaliana ( i x ) FEATURE:
    ( A ) NAME/KEY: CDS
    ( B ) LOCATION: 1..522

( x i ) SEQUENCE DESCRIPTION: SEQ ID NO:1:

```
ATG GCG GAT ACA GCT AGA GGA ACC CAT CAC GAT ATC ATC GGC AGA GAC        48
Met Ala Asp Thr Ala Arg Gly Thr His His Asp Ile Ile Gly Arg Asp
 1               5                  10                  15

CAG TAC CCG ATG ATG GGC CGA GAC CGA GAC CAG TAC CAG ATG TCC GGA        96
Gln Tyr Pro Met Met Gly Arg Asp Arg Asp Gln Tyr Gln Met Ser Gly
             20                  25                  30

CGA GGA TCT GAC TAC TCC AAG TCT AGG CAG ATT GCT AAA GCT GCA ACT       144
Arg Gly Ser Asp Tyr Ser Lys Ser Arg Gln Ile Ala Lys Ala Ala Thr
         35                  40                  45

GCT GTC ACA GCT GGT GGT TCC CTC CTT GTT CTC TCC AGC CTT ACC CTT       192
Ala Val Thr Ala Gly Gly Ser Leu Leu Val Leu Ser Ser Leu Thr Leu
     50                  55                  60

GTT GGA ACT GTC ATA GCT TTG ACT GTT GCA ACA CCT CTG CTC GTT ATC       240
Val Gly Thr Val Ile Ala Leu Thr Val Ala Thr Pro Leu Leu Val Ile
 65                  70                  75                  80

TTC AGC CCA ATC CTT GTC CCG GCT CTC ATC ACA GTT GCA CTC CTC ATC       288
Phe Ser Pro Ile Leu Val Pro Ala Leu Ile Thr Val Ala Leu Leu Ile
             85                  90                  95

ACC GGT TTT CTT TCC TCT GGA GGG TTT GGC ATT GCC GCT ATA ACC GTT       336
Thr Gly Phe Leu Ser Ser Gly Gly Phe Gly Ile Ala Ala Ile Thr Val
        100                 105                 110

TTC TCT TGG ATT TAC AAG TAC GCA ACG GGA GAG CAC CCA CAG GGA TCA       384
Phe Ser Trp Ile Tyr Lys Tyr Ala Thr Gly Glu His Pro Gln Gly Ser
    115                 120                 125

GAC AAG TTG GAC AGT GCA AGG ATG AAG TTG GGA AGC AAA GCT CAG GAT       432
Asp Lys Leu Asp Ser Ala Arg Met Lys Leu Gly Ser Lys Ala Gln Asp
130                 135                 140

CTG AAA GAC AGA GCT CAG TAC TAC GGA CAG CAA CAT ACT GGT GGG GAA       480
Leu Lys Asp Arg Ala Gln Tyr Tyr Gly Gln Gln His Thr Gly Gly Glu
145                 150                 155                 160

CAT GAC CGT GAC CGT ACT CGT GGT GGC CAG CAC ACT ACT TAA               522
His Asp Arg Asp Arg Thr Arg Gly Gly Gln His Thr Thr *
                165                 170
```

( 2 ) INFORMATION FOR SEQ ID NO:2:

( i ) SEQUENCE CHARACTERISTICS:
    ( A ) LENGTH: 173 amino acids
    ( B ) TYPE: amino acid
    ( D ) TOPOLOGY: linear ( i i ) MOLECULE TYPE: protein ( x i ) SEQUENCE DESCRIPTION: SEQ ID NO:2:

```
Met Ala Asp Thr Ala Arg Gly Thr His His Asp Ile Ile Gly Arg Asp
 1               5                  10                  15

Gln Tyr Pro Met Met Gly Arg Asp Arg Asp Gln Tyr Gln Met Ser Gly
             20                  25                  30
```

```
Arg Gly Ser Asp Tyr Ser Lys Ser Arg Gln Ile Ala Lys Ala Ala Thr
         35                  40                  45

Ala Val Thr Ala Gly Gly Ser Leu Leu Val Leu Ser Ser Leu Thr Leu
     50                  55                  60

Val Gly Thr Val Ile Ala Leu Thr Val Ala Thr Pro Leu Leu Val Ile
 65                  70                  75                  80

Phe Ser Pro Ile Leu Val Pro Ala Leu Ile Thr Val Ala Leu Leu Ile
                 85                  90                  95

Thr Gly Phe Leu Ser Ser Gly Gly Phe Gly Ile Ala Ala Ile Thr Val
                100                 105                 110

Phe Ser Trp Ile Tyr Lys Tyr Ala Thr Gly Glu His Pro Gln Gly Ser
             115                 120                 125

Asp Lys Leu Asp Ser Ala Arg Met Lys Leu Gly Ser Lys Ala Gln Asp
     130                 135                 140

Leu Lys Asp Arg Ala Gln Tyr Tyr Gly Gln Gln His Thr Gly Gly Glu
 145                 150                 155                 160

His Asp Arg Asp Arg Thr Arg Gly Gly Gln His Thr Thr
                 165                 170
```

( 2 ) INFORMATION FOR SEQ ID NO:3:

( i ) SEQUENCE CHARACTERISTICS:
        ( A ) LENGTH: 2115 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Oleosin - Hirudin Fusion ( i x ) FEATURE:
        ( A ) NAME/KEY: CDS
        ( B ) LOCATION: 862..1215

( i x ) FEATURE:
        ( A ) NAME/KEY: CDS
        ( B ) LOCATION: 1456..1833

( x i ) SEQUENCE DESCRIPTION: SEQ ID NO:3:

```
CTATACCCAA CCTCGGTCTT GGTCACACCA GGAACTCTCT GGTAAGCTAG CTCCACTCCC     60
CAGAAACAAC CGGCGCCAAA TTGCCGGAAT TGCTGACCTG AAGACGGAAC ATCATCGTCG    120
GGTCCTTGGG CGATTGCGGC GGAAGATGGG TCAGCTTGGG CTTGAGGACG AGACCCGAAT    180
CGAGTCTGTT GAAAGGTTGT TCATTGGGAT TTGTATACGG AGATTGGTCG TCGAGAGGTT    240
TGAGGGAAAG GACAAATGGG TTTGGCTCTG GAGAAAGAGA GTGCGGCTTT AGAGAGAGAA    300
TTGAGAGGTT TAGAGAGAGA TGCGGCGGCG ATGACGGGAG GAGAGACGAC GAGGACCTGC    360
ATTATCAAAG CAGTGACGTG GTGAAATTTG GAACTTTTAA GAGGCAGATA GATTTATTAT    420
TTGTATCCAT TTTCTTCATT GTTCTAGAAT GTCGCGGAAC AAATTTTAAA ACTAAATCCT    480
AAATTTTTCT AATTTTGTTG CCAATAGTGG ATATGTGGGC CGTATAGAAG GAATCTATTG    540
AAGGCCCAAA CCCATACTGA CGAGCCCAAA GGTTCGTTTT GCGTTTTATG TTTCGGTTCG    600
ATGCCAACGC CACATTCTGA GCTAGGCAAA AAACAAACGT GTCTTTGAAT AGACTCCTCT    660
CGTTAACACA TGCAGCGGCT GCATGGTGAC GCCATTAACA CGTGGCCTAC AATTGCATGA    720
TGTCTCCATT GACACGTGAC TTCTCGTCTC CTTTCTTAAT ATATCTAACA AACACTCCTA    780
CCTCTTCCAA AATATATACA CATCTTTTTG ATCAATCTCT CATTCAAAAT CTCATTCTCT    840
```

```
CTAGTAAACA AGAACAAAAA A ATG GCG GAT ACA GCT AGA GGA ACC CAT CAC        891
                       Met Ala Asp Thr Ala Arg Gly Thr His His
                        1           5                      10

GAT ATC ATC GGC AGA GAC CAG TAC CCG ATG ATG GGC CGA GAC CGA GAC        939
Asp Ile Ile Gly Arg Asp Gln Tyr Pro Met Met Gly Arg Asp Arg Asp
             15                  20                  25

CAG TAC CAG ATG TCC GGA CGA GGA TCT GAC TAC TCC AAG TCT AGG CAG        987
Gln Tyr Gln Met Ser Gly Arg Gly Ser Asp Tyr Ser Lys Ser Arg Gln
         30                  35                  40

ATT GCT AAA GCT GCA ACT GCT GTC ACA GCT GGT GGT TCC CTC CTT GTT       1035
Ile Ala Lys Ala Ala Thr Ala Val Thr Ala Gly Gly Ser Leu Leu Val
             45                  50                  55

CTC TCC AGC CTT ACC CTT GTT GGA ACT GTC ATA GCT TTG ACT GTT GCA       1083
Leu Ser Ser Leu Thr Leu Val Gly Thr Val Ile Ala Leu Thr Val Ala
         60                  65                  70

ACA CCT CTG CTC GTT ATC TTC AGC CCA ATC CTT GTC CCG GCT CTC ATC       1131
Thr Pro Leu Leu Val Ile Phe Ser Pro Ile Leu Val Pro Ala Leu Ile
 75                  80                  85                  90

ACA GTT GCA CTC CTC ATC ACC GGT TTT CTT TCC TCT GGA GGG TTT GGC       1179
Thr Val Ala Leu Leu Ile Thr Gly Phe Leu Ser Ser Gly Gly Phe Gly
             95                 100                 105

ATT GCC GCT ATA ACC GTT TTC TCT TGG ATT TAC AAG TAAGCACACA            1225
Ile Ala Ala Ile Thr Val Phe Ser Trp Ile Tyr Lys
             110                 115

TTTATCATCT TACTTCATAA TTTTGTGCAA TATGTGCATG CATGTGTTGA GCCAGTAGCT     1285

TTGGATCAAT TTTTTTGGTC GAATAACAAA TGTAACAATA AGAAATTGCA AATTCTAGGG     1345

AACATTTGGT TAACTAAATA CGAAATTTGA CCTAGCTAGC TTGAATGTGT CTGTGTATAT     1405

CATCTATATA GGTAAAATGC TTGGTATGAT ACCTATTGAT TGTGAATAGG TAC GCA       1461
                                                         Tyr Ala
                                                          1

ACG GGA GAG CAC CCA CAG GGA TCA GAC AAG TTG GAC AGT GCA AGG ATG       1509
Thr Gly Glu His Pro Gln Gly Ser Asp Lys Leu Asp Ser Ala Arg Met
         5                   10                  15

AAG TTG GGA AGC AAA GCT CAG GAT CTG AAA GAC AGA GCT CAG TAC TAC       1557
Lys Leu Gly Ser Lys Ala Gln Asp Leu Lys Asp Arg Ala Gln Tyr Tyr
         20                  25                  30

GGA CAG CAA CAT ACT GGT TGG GAA CAT GAC CGT GAC CGT ACT CGT GGT       1605
Gly Gln Gln His Thr Gly Trp Glu His Asp Arg Asp Arg Thr Arg Gly
 35                  40                  45                  50

GGC CAG CAC ACT ACT GCG ATC GAA GGG AGA ATC ACT TAC ACT GAC TGT       1653
Gly Gln His Thr Thr Ala Ile Glu Gly Arg Ile Thr Tyr Thr Asp Cys
             55                  60                  65

ACT GAA TCT GGA CAG AAC CTC TGT CTC TGT GAA GGA TCT AAC GTT TGT       1701
Thr Glu Ser Gly Gln Asn Leu Cys Leu Cys Glu Gly Ser Asn Val Cys
             70                  75                  80

GGA AAG GGA AAC AAG TGT ATC CTC GGA TCT AAC GGA AAG GGA AAC CAG       1749
Gly Lys Gly Asn Lys Cys Ile Leu Gly Ser Asn Gly Lys Gly Asn Gln
             85                  90                  95

TGT GTT ACT GGA GAA GGA ACT CCA AAC CCA GAA TCT CAC AAC AAC GGA       1797
Cys Val Thr Gly Glu Gly Thr Pro Asn Pro Glu Ser His Asn Asn Gly
100                 105                 110

GAC TTC GAA GAA ATC CCT GAA GAA TAC CTC CAG TAA GTCGACTCTA            1843
Asp Phe Glu Glu Ile Pro Glu Glu Tyr Leu Gln  *
115                 120                 125

GACGGATCTC CCGATCGTTC AAACATTTGG CAATAAAGTT TCTTAAGATT GAATCCTGTT     1903

GCCGGTCTTG CGATGATTAT CATATAATTT CTGTTGAATT ACGTTAAGCA TGTAATAATT     1963

AACATGTAAT GCATGACGTT ATTTATGAGA TGGGTTTTTA TGATTAGAGT CCCGCAATTA     2023
```

```
TACATTTAAT  ACGCGATAGA  AAACAAAATA  TAGCGCGCAA  ACTAGGATAA  ATTATCGCGC       2083

GCGGTGTCAT  CTATGTTACT  AGATCGGAAT  TC                                      2115
```

( 2 ) INFORMATION FOR SEQ ID NO:4:

( i ) SEQUENCE CHARACTERISTICS:
        ( A ) LENGTH: 118 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Ala  Asp  Thr  Ala  Arg  Gly  Thr  His  His  Asp  Ile  Ile  Gly  Arg  Asp
 1              5                        10                       15

Gln  Tyr  Pro  Met  Met  Gly  Arg  Asp  Arg  Asp  Gln  Tyr  Gln  Met  Ser  Gly
               20                   25                   30

Arg  Gly  Ser  Asp  Tyr  Ser  Lys  Ser  Arg  Gln  Ile  Ala  Lys  Ala  Ala  Thr
          35                        40                        45

Ala  Val  Thr  Ala  Gly  Gly  Ser  Leu  Leu  Val  Leu  Ser  Ser  Leu  Thr  Leu
     50                        55                        60

Val  Gly  Thr  Val  Ile  Ala  Leu  Thr  Val  Ala  Thr  Pro  Leu  Leu  Val  Ile
65                        70                   75                            80

Phe  Ser  Pro  Ile  Leu  Val  Pro  Ala  Leu  Ile  Thr  Val  Ala  Leu  Leu  Ile
                    85                        90                       95

Thr  Gly  Phe  Leu  Ser  Ser  Gly  Gly  Phe  Gly  Ile  Ala  Ala  Ile  Thr  Val
               100                      105                      110

Phe  Ser  Trp  Ile  Tyr  Lys
               115
```

( 2 ) INFORMATION FOR SEQ ID NO:5:

( i ) SEQUENCE CHARACTERISTICS:
        ( A ) LENGTH: 125 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Tyr  Ala  Thr  Gly  Glu  His  Pro  Gln  Gly  Ser  Asp  Lys  Leu  Asp  Ser  Ala
 1              5                        10                       15

Arg  Met  Lys  Leu  Gly  Ser  Lys  Ala  Gln  Asp  Leu  Lys  Asp  Arg  Ala  Gln
               20                   25                   30

Tyr  Tyr  Gly  Gln  Gln  His  Thr  Gly  Trp  Glu  His  Asp  Arg  Asp  Arg  Thr
          35                        40                        45

Arg  Gly  Gly  Gln  His  Thr  Thr  Ala  Ile  Glu  Gly  Arg  Ile  Thr  Tyr  Thr
     50                        55                        60

Asp  Cys  Thr  Glu  Ser  Gly  Gln  Asn  Leu  Cys  Leu  Cys  Glu  Gly  Ser  Asn
65                        70                        75                       80

Val  Cys  Gly  Lys  Gly  Asn  Lys  Cys  Ile  Leu  Gly  Ser  Asn  Gly  Lys  Gly
                    85                        90                       95

Asn  Gln  Cys  Val  Thr  Gly  Glu  Gly  Thr  Pro  Asn  Pro  Glu  Ser  His  Asn
               100                      105                      110

Asn  Gly  Asp  Phe  Glu  Glu  Ile  Pro  Glu  Glu  Tyr  Leu  Gln
               115                      120                      125
```

( 2 ) INFORMATION FOR SEQ ID NO:6:

( i ) SEQUENCE CHARACTERISTICS:

(A) LENGTH: 2366 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Oleosin - Metallothionein Fusion (ix) FEATURE:
(A) NAME/KEY: CDS
(B) LOCATION: 1092..1856

(xi) SEQUENCE DESCRIPTION: SEQ ID NO:6:

```
GAGCTCAAAT ACGATCTGAT ACTGATAACG TCTAGATTTT TAGGGTTAAA GCAATCAATC        60
ACCTGACGAT TCAAGGTGGT TGGATCATGA CGATTCCAGA AAACATCAAG CAAGCTCTCA       120
AAGCTACACT CTTTGGGATC ATACTGAACT CTAACAACCT CGTTATGTCC CGTAGTGCCA       180
GTACAGACAT CCTCGTAACT CGGATTATGC ACGATGCCAT GGCTATACCC AACCTCGGTC       240
TTGGTCACAC CAGGAACTCT CTGGTAAGCT AGCTCCACTC CCCAGAAACA ACCGGCGCCA       300
AATTGCCGGA ATTGCTGACC TGAAGACGGA ACATCATCGT CGGGTCCTTG GGCGATTGCG       360
GCGGAAGATG GGTCAGCTTG GGCTTGAGGA CGAGACCCGA ATCGAGTCTG TTGAAAGGTT       420
GTTCATTGGG ATTTGTATAC GGAGATTGGT CGTCGAGAGG TTTGAGGGAA AGGACAAATG       480
GGTTTGGCTC TGGAGAAAGA GAGTGCGGCT TTAGAGAGAG AATTGAGAGG TTTAGAGAGA       540
GATGCGGCGG CGATGACGGG AGGAGAGACG ACGAGGACCT GCATTATCAA AGCAGTGACG       600
TGGTGAAATT TGGAACTTTT AAGAGGCAGA TAGATTTATT ATTTGTATCC ATTTCTTCA        660
TTGTTCTAGA ATGTCGCGGA ACAAATTTTA AAACTAAATC CTAAATTTTT CTAATTTTGT       720
TGCCAATAGT GGATATGTGG GCCGTATAGA AGGAATCTAT TGAAGGCCCA AACCCATACT       780
GACGAGCCCA AAGGTTCGTT TTGCGTTTTA TGTTTCGGTT CGATGCCAAC GCCACATTCT       840
GAGCTAGGCA AAAAACAAAC GTGTCTTTGA ATAGACTCCT CTCGTTAACA CATGCAGCGG       900
CTGCATGGTG ACGCCATTAA CACGTGGCCT ACAATTGCAT GATGTCTCCA TTGACACGTG       960
ACTTCTCGTC TCCTTTCTTA ATATATCTAA CAAACACTCC TACCTCTTCC AAAATATATA      1020
CACATCTTTT TGATCAATCT CTCATTCAAA ATCTCATTCT CTCTAGTAAA CAGGATCCCC      1080
CTCGCGGCCG C ATG GCG GAT ACA GCT AGA ACC CAT CAC GAT GTC ACA AGT      1130
            Met Ala Asp Thr Ala Arg Thr His His Asp Val Thr Ser
              1               5                  10
CGA GAT CAG TAT CCC CGA GAC CGA GAC CAG TAT TCT ATG ATC GGT CGA         1178
Arg Asp Gln Tyr Pro Arg Asp Arg Asp Gln Tyr Ser Met Ile Gly Arg
         15                  20                  25
GAC CGT GAC CAG TAC TCT ATG ATG GGC CGA GAC CGA GAC CAG TAC AAC         1226
Asp Arg Asp Gln Tyr Ser Met Met Gly Arg Asp Arg Asp Gln Tyr Asn
 30                  35                  40                  45
ATG TAT GGT CGA GAC TAC TCC AAG TCT AGA CAG ATT GCT AAG GCT GTT         1274
Met Tyr Gly Arg Asp Tyr Ser Lys Ser Arg Gln Ile Ala Lys Ala Val
                 50                  55                  60
ACC GCA GTC ACG GCG GGT GGG TCC CTC CTT GTC CTC TCC AGT CTC ACC         1322
Thr Ala Val Thr Ala Gly Gly Ser Leu Leu Val Leu Ser Ser Leu Thr
             65                  70                  75
CTT GTT GGT ACT GTC ATT GCT TTG ACT GTT GCC ACT CCA CTC CTC GTT         1370
Leu Val Gly Thr Val Ile Ala Leu Thr Val Ala Thr Pro Leu Leu Val
         80                  85                  90
ATC TTT AGC CCA ATC CTC GTG CCG GCT CTC ATC ACC GTA GCA CTT CTC         1418
Ile Phe Ser Pro Ile Leu Val Pro Ala Leu Ile Thr Val Ala Leu Leu
     95                 100                 105
```

| | | | | | | | | | | | | | | | | |
|---|---|---|---|---|---|---|---|---|---|---|---|---|---|---|---|---|
| ATC | ACT | GGC | TTT | CTC | TCC | TCT | GGT | GGG | TTT | GCC | ATT | GCA | GCT | ATA | ACC | 1466 |
| Ile | Thr | Gly | Phe | Leu | Ser | Ser | Gly | Gly | Phe | Ala | Ile | Ala | Ala | Ile | Thr | |
| 110 | | | | | 115 | | | | 120 | | | | | | 125 | |
| GTC | TTC | TCC | TGG | ATC | TAT | AAG | TAC | GCA | ACG | GGA | GAG | CAC | CCA | CAG | GGG | 1514 |
| Val | Phe | Ser | Trp | Ile | Tyr | Lys | Tyr | Ala | Thr | Gly | Glu | His | Pro | Gln | Gly | |
| | | | | 130 | | | | | 135 | | | | | | 140 | |
| TCA | GAT | AAG | TTG | GAC | AGT | GCA | AGG | ATG | AAG | CTG | GGA | ACC | AAA | GCT | CAG | 1562 |
| Ser | Asp | Lys | Leu | Asp | Ser | Ala | Arg | Met | Lys | Leu | Gly | Thr | Lys | Ala | Gln | |
| | | | | 145 | | | | | 150 | | | | | 155 | | |
| GAT | ATT | AAA | GAC | AGA | GCT | CAA | TAC | TAC | GGA | CAG | CAA | CAT | ACA | GGT | GGT | 1610 |
| Asp | Ile | Lys | Asp | Arg | Ala | Gln | Tyr | Tyr | Gly | Gln | Gln | His | Thr | Gly | Gly | |
| | | 160 | | | | | 165 | | | | | 170 | | | | |
| GAG | CAT | GAC | CGT | GAC | CGT | ACT | CGT | GGT | GGC | CAG | CAC | ACT | ACT | CTC | GTT | 1658 |
| Glu | His | Asp | Arg | Asp | Arg | Thr | Arg | Gly | Gly | Gln | His | Thr | Thr | Leu | Val | |
| | 175 | | | | | 180 | | | | | 185 | | | | | |
| CCA | CGA | GGA | TCC | ATG | GAT | CCC | AAC | TGC | TCC | TGT | GCC | GCC | AGT | GAC | TCC | 1706 |
| Pro | Arg | Gly | Ser | Met | Asp | Pro | Asn | Cys | Ser | Cys | Ala | Ala | Ser | Asp | Ser | |
| 190 | | | | | 195 | | | | 200 | | | | | | 205 | |
| TGC | ACC | TGC | GCC | GGC | TCC | TGC | AAG | TGC | AAA | GAG | TGC | AAA | TGC | ACC | TCC | 1754 |
| Cys | Thr | Cys | Ala | Gly | Ser | Cys | Lys | Cys | Lys | Glu | Cys | Lys | Cys | Thr | Ser | |
| | | | | 210 | | | | | 215 | | | | | 220 | | |
| TGC | AAG | AAA | AGC | TGC | TGC | TCC | TGC | TGT | CCT | GTG | GGC | TGT | GCC | AAG | TGT | 1802 |
| Cys | Lys | Lys | Ser | Cys | Cys | Ser | Cys | Cys | Pro | Val | Gly | Cys | Ala | Lys | Cys | |
| | | | 225 | | | | | 230 | | | | | 235 | | | |
| GCC | CAG | GGC | TGC | ATC | TGC | AAA | GGG | GCG | TCG | GAC | AAG | TGC | AGC | TGC | TGT | 1850 |
| Ala | Gln | Gly | Cys | Ile | Cys | Lys | Gly | Ala | Ser | Asp | Lys | Cys | Ser | Cys | Cys | |
| | | 240 | | | | | 245 | | | | | 250 | | | | |
| GCC | TGA | GCGGCCGCGA | | GGGCTGCAGA | | ATGAGTTCCA | | AGATGGTTTG | | TGACGAAGTT | | | | | | 1906 |
| Ala | * | | | | | | | | | | | | | | | |
| | 255 | | | | | | | | | | | | | | | |

| | | | |
|---|---|---|---|
| AGTTGGTTGT TTTTATGGAA CTTTGTTTAA GCTTGTAATG TGGAAAGAAC GTGTGGCTTT | 1966 |
| GTGGTTTTTA AATGTTGGTG AATAAAGATG TTTCCTTTGG ATTAACTAGT ATTTTCCTA | 2026 |
| TTGGTTTCAT GGTTTTAGCA CACAACATTT TAAATATGCT GTTAGATGAT ATGCTGCCTG | 2086 |
| CTTTATTATT TACTTACCCC TCACCTTCAG TTTCAAAGTT GTTGCAATGA CTCTGTGTAG | 2146 |
| TTTAAGATCG AGTGAAAGTA GATTTGTCT ATATTTATTA GGGGTATTTG ATATGCTAAT | 2206 |
| GGTAAACATG GTTTATGACA GCGTACTTTT TTGGTTATGG TGTTGACGTT TCCTTTTAAA | 2266 |
| CATTATAGTA GCGTCCTTGG TCTGTGTTCA TTGGTTGAAC AAAGGCACAC TCACTTGGAG | 2326 |
| ATGCCGTCTC CACTGATATT TGAACAAAGA ATTCGGTACC | 2366 |

(2) INFORMATION FOR SEQ ID NO:7:

(i) SEQUENCE CHARACTERISTICS:
        (A) LENGTH: 254 amino acids
        (B) TYPE: amino acid
        (D) TOPOLOGY: linear (ii) MOLECULE TYPE: protein (xi) SEQUENCE DESCRIPTION: SEQ ID NO:7:

| | | | | | | | | | | | | | | |
|---|---|---|---|---|---|---|---|---|---|---|---|---|---|---|
| Met | Ala | Asp | Thr | Ala | Arg | Thr | His | His | Asp | Val | Thr | Ser | Arg | Asp | Gln |
| 1 | | | | 5 | | | | | 10 | | | | | 15 | |
| Tyr | Pro | Arg | Asp | Arg | Asp | Gln | Tyr | Ser | Met | Ile | Gly | Arg | Asp | Arg | Asp |
| | | | 20 | | | | | 25 | | | | | 30 | | |
| Gln | Tyr | Ser | Met | Met | Gly | Arg | Asp | Arg | Asp | Gln | Tyr | Asn | Met | Tyr | Gly |
| | | | 35 | | | | | 40 | | | | | 45 | | |
| Arg | Asp | Tyr | Ser | Lys | Ser | Arg | Gln | Ile | Ala | Lys | Ala | Val | Thr | Ala | Val |
| | | 50 | | | | | 55 | | | | | 60 | | | |

```
Thr  Ala  Gly  Gly  Ser  Leu  Leu  Val  Leu  Ser  Ser  Leu  Thr  Leu  Val  Gly
 65                  70                  75                       80

Thr  Val  Ile  Ala  Leu  Thr  Val  Ala  Thr  Pro  Leu  Leu  Val  Ile  Phe  Ser
               85                       90                       95

Pro  Ile  Leu  Val  Pro  Ala  Leu  Ile  Thr  Val  Ala  Leu  Leu  Ile  Thr  Gly
              100                      105                      110

Phe  Leu  Ser  Ser  Gly  Gly  Phe  Ala  Ile  Ala  Ala  Ile  Thr  Val  Phe  Ser
              115                      120                      125

Trp  Ile  Tyr  Lys  Tyr  Ala  Thr  Gly  Glu  His  Pro  Gln  Gly  Ser  Asp  Lys
         130                      135                      140

Leu  Asp  Ser  Ala  Arg  Met  Lys  Leu  Gly  Thr  Lys  Ala  Gln  Asp  Ile  Lys
145                      150                      155                      160

Asp  Arg  Ala  Gln  Tyr  Tyr  Gly  Gln  Gln  His  Thr  Gly  Gly  Glu  His  Asp
              165                      170                      175

Arg  Asp  Arg  Thr  Arg  Gly  Gly  Gln  His  Thr  Thr  Leu  Val  Pro  Arg  Gly
              180                      185                      190

Ser  Met  Asp  Pro  Asn  Cys  Ser  Cys  Ala  Ala  Ser  Asp  Ser  Cys  Thr  Cys
              195                      200                      205

Ala  Gly  Ser  Cys  Lys  Cys  Lys  Glu  Cys  Lys  Cys  Thr  Ser  Cys  Lys  Lys
         210                      215                      220

Ser  Cys  Cys  Ser  Cys  Cys  Pro  Val  Gly  Cys  Ala  Lys  Cys  Ala  Gln  Gly
225                      230                      235                      240

Cys  Ile  Cys  Lys  Gly  Ala  Ser  Asp  Lys  Cys  Ser  Cys  Cys  Ala
              245                      250                      255
```

( 2 ) INFORMATION FOR SEQ ID NO:8:

( i ) SEQUENCE CHARACTERISTICS:
        ( A ) LENGTH: 297 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: IgG Hinge Primers ( i x ) FEATURE:
        ( A ) NAME/KEY: CDS
        ( B ) LOCATION: 10..297

( x i ) SEQUENCE DESCRIPTION: SEQ ID NO:8:

```
GGATCCATG  AAG  CCC  AGC  AAC  ACC  AAG  GTG  GAC  AAG  AGA  GTT  GAG  CTC         48
           Lys  Pro  Ser  Asn  Thr  Lys  Val  Asp  Lys  Arg  Val  Glu  Leu
            1              5                        10

AAA  ACC  CCA  CTT  GGT  GAC  ACA  ACT  CAC  ACA  TGC  CCA  CGG  TGC  CCA  GAG     96
Lys  Thr  Pro  Leu  Gly  Asp  Thr  Thr  His  Thr  Cys  Pro  Arg  Cys  Pro  Glu
          15                      20                      25

CCC  AAA  TCT  TGT  GAC  ACA  CCT  CCC  CCG  TGC  CCA  CGG  TGC  CCA  GAG  CCC    144
Pro  Lys  Ser  Cys  Asp  Thr  Pro  Pro  Pro  Cys  Pro  Arg  Cys  Pro  Glu  Pro
 30                      35                      40                       45

AAA  TCT  TGT  GAC  ACA  CCT  CCC  CCA  TGC  CCA  CGG  TGC  CCA  GAG  CCC  AAA    192
Lys  Ser  Cys  Asp  Thr  Pro  Pro  Pro  Cys  Pro  Arg  Cys  Pro  Glu  Pro  Lys
                    50                      55                       60

TCT  TGT  GAC  ACA  CCT  CCC  CCG  TGC  CCA  AGG  TGC  CCA  GCA  CCT  GAA  CTC    240
Ser  Cys  Asp  Thr  Pro  Pro  Pro  Cys  Pro  Arg  Cys  Pro  Ala  Pro  Glu  Leu
               65                      70                       75

CTG  GGA  GGA  CCG  TCA  GTC  TTC  CTC  TTC  CCC  CCA  AAA  CCC  ATC  GAA  GGT    288
Leu  Gly  Gly  Pro  Ser  Val  Phe  Leu  Phe  Pro  Pro  Lys  Pro  Ile  Glu  Gly
 80                      85                      90
```

```
CGT GGA TCC                                                              297
Arg Gly Ser
     95
```

( 2 ) INFORMATION FOR SEQ ID NO:9:

( i ) SEQUENCE CHARACTERISTICS:
        ( A ) LENGTH: 96 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

```
Lys Pro Ser Asn Thr Lys Val Asp Lys Arg Val Glu Leu Lys Thr Pro
 1           5                  10                  15

Leu Gly Asp Thr Thr His Thr Cys Pro Arg Cys Pro Glu Pro Lys Ser
            20                  25                  30

Cys Asp Thr Pro Pro Pro Cys Pro Arg Cys Pro Glu Pro Lys Ser Cys
            35                  40                  45

Asp Thr Pro Pro Pro Cys Pro Arg Cys Pro Glu Pro Lys Ser Cys Asp
        50                  55                  60

Thr Pro Pro Pro Cys Pro Arg Cys Pro Ala Pro Glu Leu Leu Gly Gly
 65                 70                  75                  80

Pro Ser Val Phe Leu Phe Pro Pro Lys Pro Ile Glu Gly Arg Gly Ser
                85                  90                  95
```

( 2 ) INFORMATION FOR SEQ ID NO:10:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Primer IgG001

( x i ) SEQUENCE DESCRIPTION: SEQ ID NO:10:

```
GGATCCATGA AGCCCAGCAA CACCAAG                                             27
```

( 2 ) INFORMATION FOR SEQ ID NO:11:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Primer IgG002

( x i ) SEQUENCE DESCRIPTION: SEQ ID NO:11:

```
GGATCCACGA CCTTCGATGG GTTTTGGGGG GAAGAG                                   36
```

( 2 ) INFORMATION FOR SEQ ID NO:12:

( i ) SEQUENCE CHARACTERISTICS:
        ( A ) LENGTH: 804 base pairs
        ( B ) TYPE: nucleic acid
        ( C ) STRANDEDNESS: single
        ( D ) TOPOLOGY: linear ( i i ) MOLECULE TYPE: cDNA (v i) ORIGINAL SOURCE:
    (A) ORGANISM: Protein A Primers (i x) FEATURE:
    (A) NAME/KEY: CDS
    (B) LOCATION: 5..796

(x i) SEQUENCE DESCRIPTION: SEQ ID NO:12:

| | | | | | | | | | | | | | | | | |
|---|---|---|---|---|---|---|---|---|---|---|---|---|---|---|---|---|
| CTCC | ATG | GAT | CAA | CGC | AAT | GGT | TTT | ATC | CAA | AGC | CTT | AAA | GAT | GAT | CCA | 49 |
| | Met | Asp | Gln | Arg | Asn | Gly | Phe | Ile | Gln | Ser | Leu | Lys | Asp | Asp | Pro | |
| | 1 | | | | 5 | | | | | 10 | | | | | 15 | |
| AGC | CAA | AGT | GCT | AAC | GTT | TTA | GGT | GAA | GCT | CAA | AAA | CTT | AAT | GAC | TCT | 97 |
| Ser | Gln | Ser | Ala | Asn | Val | Leu | Gly | Glu | Ala | Gln | Lys | Leu | Asn | Asp | Ser | |
| | | | | 20 | | | | | 25 | | | | | 30 | | |
| CAA | GCT | CCA | AAA | GCT | GAT | GCG | CAA | CAA | AAT | AAC | TTC | AAC | AAA | GAT | CAA | 145 |
| Gln | Ala | Pro | Lys | Ala | Asp | Ala | Gln | Gln | Asn | Asn | Phe | Asn | Lys | Asp | Gln | |
| | | | 35 | | | | | 40 | | | | | 45 | | | |
| CAA | AGC | GCC | TTC | TAT | GAA | ATC | TTG | AAC | ATG | CCT | AAC | TTA | AAC | GAA | GCG | 193 |
| Gln | Ser | Ala | Phe | Tyr | Glu | Ile | Leu | Asn | Met | Pro | Asn | Leu | Asn | Glu | Ala | |
| | | 50 | | | | | 55 | | | | | 60 | | | | |
| CAA | CGT | AAC | GGC | TTC | ATT | CAA | AGT | CTT | AAA | GAC | GAC | CCA | AGC | CAA | AGC | 241 |
| Gln | Arg | Asn | Gly | Phe | Ile | Gln | Ser | Leu | Lys | Asp | Asp | Pro | Ser | Gln | Ser | |
| | 65 | | | | | 70 | | | | | 75 | | | | | |
| ACT | AAC | GTT | TTA | GGT | GAA | GCT | AAA | AAA | TTA | AAC | GAA | TCT | CAA | GCA | CCG | 289 |
| Thr | Asn | Val | Leu | Gly | Glu | Ala | Lys | Lys | Leu | Asn | Glu | Ser | Gln | Ala | Pro | |
| 80 | | | | | 85 | | | | | 90 | | | | | 95 | |
| AAA | GCT | GAT | AAC | AAT | TTC | AAC | AAA | GAA | CAA | CAA | AAT | GCT | TTC | TAT | GAA | 337 |
| Lys | Ala | Asp | Asn | Asn | Phe | Asn | Lys | Glu | Gln | Gln | Asn | Ala | Phe | Tyr | Glu | |
| | | | | 100 | | | | | 105 | | | | | 110 | | |
| ATC | TTG | AAT | ATG | CCT | AAC | TTA | AAC | GAA | GAA | CAA | CGC | AAT | GGT | TTC | ATC | 385 |
| Ile | Leu | Asn | Met | Pro | Asn | Leu | Asn | Glu | Glu | Gln | Arg | Asn | Gly | Phe | Ile | |
| | | | 115 | | | | | 120 | | | | | 125 | | | |
| CAA | AGC | TTA | AAA | GAT | GAC | CCA | AGC | CAA | AGT | GCT | AAC | CTA | TTG | TCA | GAA | 433 |
| Gln | Ser | Leu | Lys | Asp | Asp | Pro | Ser | Gln | Ser | Ala | Asn | Leu | Leu | Ser | Glu | |
| | | 130 | | | | | 135 | | | | | 140 | | | | |
| GCT | AAA | AAG | TTA | AAT | GAA | TCT | CAA | GCA | CCG | AAA | GCG | GAT | AAC | AAA | TTC | 481 |
| Ala | Lys | Lys | Leu | Asn | Glu | Ser | Gln | Ala | Pro | Lys | Ala | Asp | Asn | Lys | Phe | |
| | 145 | | | | | 150 | | | | | 155 | | | | | |
| AAC | AAA | GAA | CAA | CAA | AAT | GCT | TTC | TAT | GAA | ATC | TTA | CAT | TTA | CCT | AAC | 529 |
| Asn | Lys | Glu | Gln | Gln | Asn | Ala | Phe | Tyr | Glu | Ile | Leu | His | Leu | Pro | Asn | |
| 160 | | | | | 165 | | | | | 170 | | | | | 175 | |
| TTA | AAC | GAA | GAA | CAA | CGC | AAT | GGT | TTC | ATC | CAA | AGC | CTA | AAA | GAT | GAC | 577 |
| Leu | Asn | Glu | Glu | Gln | Arg | Asn | Gly | Phe | Ile | Gln | Ser | Leu | Lys | Asp | Asp | |
| | | | | 180 | | | | | 185 | | | | | 190 | | |
| CCA | AGC | CAA | AGC | GCT | AAC | CTT | TTA | GCA | GAA | GCT | AAA | AAG | CTA | AAT | GAT | 625 |
| Pro | Ser | Gln | Ser | Ala | Asn | Leu | Leu | Ala | Glu | Ala | Lys | Lys | Leu | Asn | Asp | |
| | | | 195 | | | | | 200 | | | | | 205 | | | |
| GCT | CAA | GCA | CCA | AAA | GCT | GAC | AAC | AAA | TTC | AAC | AAA | GAA | CAA | CAA | AAT | 673 |
| Ala | Gln | Ala | Pro | Lys | Ala | Asp | Asn | Lys | Phe | Asn | Lys | Glu | Gln | Gln | Asn | |
| | | 210 | | | | | 215 | | | | | 220 | | | | |
| GCT | TTC | TAT | GAA | ATT | TTA | CAT | TTA | CCT | AAC | TTA | ACT | GAA | GAA | CAA | CGT | 721 |
| Ala | Phe | Tyr | Glu | Ile | Leu | His | Leu | Pro | Asn | Leu | Thr | Glu | Glu | Gln | Arg | |
| | 225 | | | | | 230 | | | | | 235 | | | | | |
| AAC | GGC | TTC | ATC | CAA | AGC | CTT | AAA | GAC | GAT | CCG | GGG | AAT | TCC | CGG | GGA | 769 |
| Asn | Gly | Phe | Ile | Gln | Ser | Leu | Lys | Asp | Asp | Pro | Gly | Asn | Ser | Arg | Gly | |
| 240 | | | | | 245 | | | | | 250 | | | | | 255 | |
| TCC | GTC | GAC | CTG | CAG | ATA | ACA | AAT | TAG | AAGCTTGC | | | | | | | 804 |
| Ser | Val | Asp | Leu | Gln | Ile | Thr | Asn | * | | | | | | | | |
| | | | | 260 | | | | | | | | | | | | |

(2) INFORMATION FOR SEQ ID NO:13:

( i ) SEQUENCE CHARACTERISTICS:
  ( A ) LENGTH: 263 amino acids
  ( B ) TYPE: amino acid
  ( D ) TOPOLOGY: linear ( i i ) MOLECULE TYPE: protein ( x i ) SEQUENCE DESCRIPTION: SEQ ID NO:13:

| Met | Asp | Gln | Arg | Asn | Gly | Phe | Ile | Gln | Ser | Leu | Lys | Asp | Asp | Pro | Ser |
|---|---|---|---|---|---|---|---|---|---|---|---|---|---|---|---|
| 1 | | | | 5 | | | | | 10 | | | | | 15 | |

| Gln | Ser | Ala | Asn | Val | Leu | Gly | Glu | Ala | Gln | Lys | Leu | Asn | Asp | Ser | Gln |
|---|---|---|---|---|---|---|---|---|---|---|---|---|---|---|---|
| | | | 20 | | | | 25 | | | | | 30 | | | |

| Ala | Pro | Lys | Ala | Asp | Ala | Gln | Gln | Asn | Asn | Phe | Asn | Lys | Asp | Gln | Gln |
|---|---|---|---|---|---|---|---|---|---|---|---|---|---|---|---|
| | | 35 | | | | | 40 | | | | | 45 | | | |

| Ser | Ala | Phe | Tyr | Glu | Ile | Leu | Asn | Met | Pro | Asn | Leu | Asn | Glu | Ala | Gln |
|---|---|---|---|---|---|---|---|---|---|---|---|---|---|---|---|
| | 50 | | | | | 55 | | | | | 60 | | | | |

| Arg | Asn | Gly | Phe | Ile | Gln | Ser | Leu | Lys | Asp | Asp | Pro | Ser | Gln | Ser | Thr |
|---|---|---|---|---|---|---|---|---|---|---|---|---|---|---|---|
| 65 | | | | | 70 | | | | | 75 | | | | | 80 |

| Asn | Val | Leu | Gly | Glu | Ala | Lys | Lys | Leu | Asn | Glu | Ser | Gln | Ala | Pro | Lys |
|---|---|---|---|---|---|---|---|---|---|---|---|---|---|---|---|
| | | | | 85 | | | | | 90 | | | | | 95 | |

| Ala | Asp | Asn | Asn | Phe | Asn | Lys | Glu | Gln | Gln | Asn | Ala | Phe | Tyr | Glu | Ile |
|---|---|---|---|---|---|---|---|---|---|---|---|---|---|---|---|
| | | | 100 | | | | | 105 | | | | | 110 | | |

| Leu | Asn | Met | Pro | Asn | Leu | Asn | Glu | Gln | Arg | Asn | Gly | Phe | Ile | Gln |
|---|---|---|---|---|---|---|---|---|---|---|---|---|---|---|
| | | 115 | | | | | 120 | | | | | 125 | | |

| Ser | Leu | Lys | Asp | Asp | Pro | Ser | Gln | Ser | Ala | Asn | Leu | Leu | Ser | Glu | Ala |
|---|---|---|---|---|---|---|---|---|---|---|---|---|---|---|---|
| | 130 | | | | | 135 | | | | | 140 | | | | |

| Lys | Lys | Leu | Asn | Glu | Ser | Gln | Ala | Pro | Lys | Ala | Asp | Asn | Lys | Phe | Asn |
|---|---|---|---|---|---|---|---|---|---|---|---|---|---|---|---|
| 145 | | | | | 150 | | | | | 155 | | | | | 160 |

| Lys | Glu | Gln | Gln | Asn | Ala | Phe | Tyr | Glu | Ile | Leu | His | Leu | Pro | Asn | Leu |
|---|---|---|---|---|---|---|---|---|---|---|---|---|---|---|---|
| | | | | 165 | | | | | 170 | | | | | 175 | |

| Asn | Glu | Glu | Gln | Arg | Asn | Gly | Phe | Ile | Gln | Ser | Leu | Lys | Asp | Asp | Pro |
|---|---|---|---|---|---|---|---|---|---|---|---|---|---|---|---|
| | | | 180 | | | | | 185 | | | | | 190 | | |

| Ser | Gln | Ser | Ala | Asn | Leu | Leu | Ala | Glu | Ala | Lys | Lys | Leu | Asn | Asp | Ala |
|---|---|---|---|---|---|---|---|---|---|---|---|---|---|---|---|
| | | 195 | | | | | 200 | | | | | 205 | | | |

| Gln | Ala | Pro | Lys | Ala | Asp | Asn | Lys | Phe | Asn | Lys | Glu | Gln | Gln | Asn | Ala |
|---|---|---|---|---|---|---|---|---|---|---|---|---|---|---|---|
| | 210 | | | | | 215 | | | | | 220 | | | | |

| Phe | Tyr | Glu | Ile | Leu | His | Leu | Pro | Asn | Leu | Thr | Glu | Glu | Gln | Arg | Asn |
|---|---|---|---|---|---|---|---|---|---|---|---|---|---|---|---|
| 225 | | | | | 230 | | | | | 235 | | | | | 240 |

| Gly | Phe | Ile | Gln | Ser | Leu | Lys | Asp | Asp | Pro | Gly | Asn | Ser | Arg | Gly | Ser |
|---|---|---|---|---|---|---|---|---|---|---|---|---|---|---|---|
| | | | | 245 | | | | | 250 | | | | | 255 | |

| Val | Asp | Leu | Gln | Ile | Thr | Asn |
|---|---|---|---|---|---|---|
| | | | 260 | | | |

( 2 ) INFORMATION FOR SEQ ID NO:14:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Primer Bk 266

( x i ) SEQUENCE DESCRIPTION: SEQ ID NO:14:

CTCCATGGAT CAACGCAATG GTTTATC              27

(2) INFORMATION FOR SEQ ID NO:15:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Primer Bk267

(xi) SEQUENCE DESCRIPTION: SEQ ID NO:15:

GCAAGCTTCT AATTTGTTAT CTGCAGGTC    29